United States Patent
Yang et al.

(10) Patent No.: US 10,182,993 B2
(45) Date of Patent: Jan. 22, 2019

(54) COMPOSITIONS FOR COLONIC DELIVERY OF DRUGS

(71) Applicant: PATHEON SOFTGELS INC, High Point, NC (US)

(72) Inventors: Chue Hue Yang, Greensboro, NC (US); Tatyana Dyakonov, Greensboro, NC (US); George Vamvakas, Greensboro, NC (US); Aqeel A. Fatmi, High Point, NC (US)

(73) Assignee: Patheon Softgels Inc., High Point, NC (US)

( * ) Notice: Subject to any disclaimer, the term of this patent is extended or adjusted under 35 U.S.C. 154(b) by 0 days.

(21) Appl. No.: 15/090,628

(22) Filed: Apr. 5, 2016

(65) Prior Publication Data

US 2016/0287525 A1  Oct. 6, 2016

Related U.S. Application Data

(60) Provisional application No. 62/143,426, filed on Apr. 6, 2015.

(51) Int. Cl.
*A61K 9/48* (2006.01)
*A61K 31/606* (2006.01)

(52) U.S. Cl.
CPC .......... *A61K 9/4866* (2013.01); *A61K 9/4825* (2013.01); *A61K 9/4858* (2013.01); *A61K 9/4875* (2013.01); *A61K 31/606* (2013.01)

(58) Field of Classification Search
None
See application file for complete search history.

(56) References Cited

U.S. PATENT DOCUMENTS

| | | |
|---|---|---|
| 4,190,176 A | 2/1980 | Hascoe |
| 4,693,895 A | 9/1987 | Wong |
| 4,904,474 A | 2/1990 | Wong |
| 5,146,730 A | 9/1992 | Dietel |
| 5,171,580 A | 12/1992 | Lino |
| 5,407,682 A | 4/1995 | Wilding |
| 5,420,197 A | 5/1995 | Lorenz |
| 5,459,983 A | 10/1995 | Dietel |
| 5,482,718 A | 1/1996 | Shah |
| 5,637,319 A | 6/1997 | Takada |
| 5,744,166 A | 4/1998 | Illum |
| 6,039,975 A | 3/2000 | Railkar |
| 6,231,888 B1 | 5/2001 | Flashner |
| 6,248,362 B1 | 6/2001 | Yamada |
| 6,319,518 B1 | 11/2001 | Pai |
| 6,465,626 B1 | 10/2002 | Illum |
| 6,482,516 B1 | 11/2002 | Dietel |
| 6,506,407 B2 | 1/2003 | Masataka |
| 7,485,294 B2 | 2/2009 | Fattal |
| 7,833,765 B2 | 11/2010 | Fattal |
| 8,685,445 B2 | 4/2014 | Hassan |
| 2005/0249716 A1 | 11/2005 | Fattal |
| 2006/0115527 A1 | 6/2006 | Nachiappan |
| 2006/0165778 A1 | 7/2006 | Hassan |
| 2006/0188563 A1 | 8/2006 | Takaaki |
| 2007/0053868 A1 | 3/2007 | Aqeel |
| 2008/0081060 A1 | 4/2008 | Bumgardner |
| 2009/0162339 A1 | 6/2009 | Bourgeois |
| 2010/0209520 A1 | 8/2010 | Kubo |
| 2010/0239685 A1 | 9/2010 | Kwak |
| 2011/0244034 A1 | 10/2011 | Dhaliwal |
| 2011/0250238 A1 | 10/2011 | Spreafico |
| 2012/0301546 A1* | 11/2012 | Hassan ............... A61K 31/00 424/465 |
| 2014/0271861 A1* | 9/2014 | Emanuel ............ A61K 9/1271 424/484 |

FOREIGN PATENT DOCUMENTS

WO    WO 2004/084869    * 10/2004

OTHER PUBLICATIONS

Elbary et al. (AAPS PharmSciTech, 12(4), 1454-1464, 2011) Once daily, High-Dose Mesalazine . . . .*
Lee et al. (Arch Pharm Res 31(8), 1023-1028, 2008) Effect of Poloxamer . . . .*

* cited by examiner

*Primary Examiner* — Tigabu Kassa
(74) *Attorney, Agent, or Firm* — Brinks Gilson & Lione

(57) ABSTRACT

Described herein are controlled release oral pharmaceutical compositions for delivering active pharmaceutical ingredients to the colon and methods for making the same. In particular, an oral pharmaceutical composition comprising a soft capsule and a controlled release matrix for delivering active pharmaceutical ingredients to the colon are described.

4 Claims, 2 Drawing Sheets

COMPOSITIONS FOR COLONIC DELIVERY OF DRUGS

CROSS REFERENCE TO RELATED APPLICATIONS

This application claims priority to U.S. Provisional Patent Application No. 62/143,426, filed on Apr. 6, 2015, which is incorporated herein in its entirety by express reference thereto.

TECHNICAL FIELD

Described herein are controlled release oral pharmaceutical compositions for delivering active pharmaceutical ingredients to the colon and methods for making the same. In particular, an oral pharmaceutical composition comprising a soft capsule and a controlled release matrix for delivering active pharmaceutical ingredients to the colon are described.

BACKGROUND

Colonic delivery refers to the targeted delivery of drugs into the lower GI tract (i.e., colon) which is advantageous for localized treatment of several colonic diseases, namely inflammatory bowel diseases (Crohn's disease and ulcerative colitis), irritable bowel syndrome, and colon cancer. Other potential applications of colonic delivery include chronotherapy of diseases such as asthma, hypertension, cardiac arrhythmias, arthritis, or inflammation, which are affected by circadian biorhythms, prophylaxis of colon cancer and treatment of nicotine addiction.

The colon also offers an opportunistic site for oral delivery of vaccines because it is rich in lymphoid tissue making possible the uptake of antigens through the colonic mucosa leading to rapid and local production of antibodies. There is also an interest in colonic delivery for improving the oral bioavailability of drugs that are substrates of cytochrome P450 3A. Increasing bioavailability via a colonic formulation approach has also been found to be effective in minimizing unwanted side-effects. Also, for drugs with high first pass hepatic metabolism the colon is an attractive target for delivery into the lymphatic system thus by-passing the liver.

Formulations for colonic delivery are also suitable for delivery of drugs that are polar and/or susceptible to chemical and enzymatic degradation in the upper GI tract, in particular, proteins and peptides, such as insulin, calcitonin, and vasopressin.

However, colonic specific delivery presents numerous challenges due to the physiology of the gastro-intestinal tract. One potential issue is that the colon has a distal location and the GI tract has numerous physiological gradients (e.g., pH, enzymes, absorption barrier, etc). Other issues stem from the large differences in the absorptive surface area of the small intestine (e.g., greater than about 120 m$^2$) and the colon (e.g., about 0.25 m$^2$). In addition to the relatively low surface area, there is a limited amount of fluid available for drug dissolution within the colon. Drug stability within the colon remains a problem as numerous drugs have been shown to be metabolised by colonic microbiota and the proteolytic enzymatic activity of the colon is high. Furthermore, there are difficulties designing a precise trigger for drug release within the colon.

Several approaches have been developed to circumvent some of these colonic delivery problems. First approaches utilize enteric coatings on tablets or capsules to bypass the delivery to the stomach; however, the long transit time through the small intestine and lag times at the ileo-cecal junction may prevent accurate release of enterically coated drug formulations. Another approach has been to utilize time dependent release systems with swellable methyl cellulose coatings. These colonic delivery systems can be problematic due to variable gastric release times and rapid transit due to frequent diarrhea in patients with inflammatory bowel disease (IBD).

More integrated approaches have been developed, for example, U.S. Pat. No. 4,190,176 describes an Azo-prodrug system for colonic delivery. The Azo moeity reduces the absorption of the drug in the small intestine. Release within the colon relies upon bacterially produced enzymes which cleave the Azo linkage of the prodrug, allowing it to be absorbed. Other chemical linkages have been used, including amide linkages, glycosidic linkages, and glucoronide linkages. However, this approach can be limiting as the drug/prodrug formulation is highly dependent upon available functional groups on the drug for chemical linkage and prodrugs are new chemical entities requiring time-consuming in vivo evaluation. A similar approach described in U.S. Pat. No. 6,506,407 uses bacterially initiated degradation of a polysaccharide and subsequent localized pH changes for degradation of an enteric polymer coating.

Another approach described in U.S. Pat. No. 5,637,319 for colonic drug delivery is because the colon can exhibit higher pressures on capsules due to peristalsis and increased friction due to lower moisture compared to the small intestine. These type of pressure controlled drug-delivery system utilizes capsules coated with a water-insoluble polymer that prevent drug release in the stomach and small intestine; once the large intestine is reached, the increased pressure results in the breakdown of the capsule. This pressure based strategy can be limiting due to increased drug release lag times, and the dependency of a functional colon (e.g., specifically needed pressures and moisture contents). These systems are limited, as discussed above, in patients with diarrhea or gastro-intestinal problems, especially those patients having IBD.

U.S. Pat. Nos. 4,693,895 and 4,904,474 describe a complex osmotic pressure release system consisting of a hard gelatin capsule comprising an active ingredient in multiple enterically coated subunits for colonic delivery.

Most all of these systems rely on enterically coated tablets or capsules to bypass the stomach, which are produced by a film-coating process, where a thin film layer of acid-insoluble (enteric) polymer is accumulated on the surface of a pre-manufactured dosage form. The enteric coating method involves the spraying of an aqueous or organic solution or a suspension of enteric polymers onto tumbling or moving tablets or capsules, accompanied by drying using hot air.

Enteric dosage forms made by coating suffer from various process-related problems and defects that affect their performance or appearance. For example, "orange peel" surface formation, also known as surface roughness, mottling, or lack of surface homogeneity may result. In addition, coat integrity failure may occur, such as in cases of cracking or flaking of the coating. All coatings present inherent problems, including possible uneven distribution of the coating ingredients, which can easily happen under the multivariate coating process. These failures of enteric coatings reduce the effectiveness of said coating in preventing painful and often harmful gastric and esophageal disturbances.

The foregoing problems of enteric coatings are shared by all enteric dosage forms such as tablets and capsules. However, the problems faced during coating of capsules are even more critical, due to the delicate and heat sensitive nature of the soft elastic capsule shell. Both hard and soft capsules can easily undergo agglomeration and distortion due to the heat-sensitive shell composition. Moreover, the smoothness and elasticity of the capsule surface make it difficult to form an intact adhering enteric coat without careful sub-coating steps to improve the surface for coating. A further disadvantage of enteric coating for soft capsules is the loss of the normally shiny and clear appearance of capsule gelatin shells. The elegant, clear gelatin shell has been a significant reason for soft capsule popularity and acceptance. In addition to the undesirable surface texture modifications usually caused by coating, most accepted aqueous enteric polymer preparations result in opaque capsules.

These prior approaches for colonic delivery are complex and rely on numerous variables for accurate release (e.g., time, drug chemical modification, enzymatic cleavage, peristaltic pressure, etc.). Furthermore, inconsistencies in enteric polymer coatings as described above can lead to inconsistent drug release and efficacy. Therefore, there is a need for a pharmaceutical composition that can be efficiently manufactured, has the popular characteristics of a clear soft gelatin capsule that can be taken orally, and demonstrates a consistent and robust delivery to the colon.

SUMMARY

One embodiment described herein is an oral pharmaceutical composition comprising a controlled release matrix comprising: (a) at least one lipid or lipophilic vehicle; (b) at least one hydrophilic polymer; (c) at least one hygroscopic polymer; (d) at least one non-ionic surfactant; and (e) at least one active pharmaceutical ingredient, wherein the matrix dissolves in the colon and is encapsulated in a soft capsule shell. In one aspect described herein, the lipid or lipophilic vehicle comprises about 25% to about 90% of the total matrix mass. In another aspect described herein, the at least one hygroscopic polymer comprises from about 1% to about 10% of the total matrix mass. In another aspect described herein, the at least one hydrophilic polymer comprises about 1% to about 20% of the total matrix mass. In another aspect described herein, the non-ionic surfactant comprises from about 1% to about 15% of the total matrix mass. In another aspect described herein, the at least one active pharmaceutical ingredient comprises about 1% to about 50% of the total matrix mass. In another aspect described herein, the ratio of the active pharmaceutical ingredient percent mass to the matrix percent mass is about 1:100 to about 1:1. In another aspect described herein, the lipid or lipophilic vehicle comprises at least one liquid lipid or lipophilic vehicle and at least one semisolid lipid or lipophilic vehicle. In another aspect described herein, the liquid lipid or lipophilic vehicle comprises: olive oil, sunflower oil, canola oil, palmitoleic acid, oleic acid, myristoleic acid, linoleic acid, arachidonic acid, paraffin oil, or mineral oil. In another aspect described herein, the lipid or lipophilic vehicle comprises olive oil, soybean oil, or oleic acid. In another aspect described herein, the semisolid lipid or lipophilic vehicle comprises one or more of: polyethylene glycol glyceride ester, paraffin wax, or bee's wax. In another aspect described herein, the lipid or lipophilic vehicle comprises soybean oil, a polyethylene glycol glyceride ester, and bee's wax. In another aspect described herein, the polyethylene glycol glyceride esters comprise glycerol esters of saturated fatty acids of about 8 to about 18 carbon molecules in length. In another aspect described herein, the lipid or lipophilic vehicle comprises about 48% to about 52% of the total matrix mass. In another aspect described herein, the hygroscopic polymer comprises one or more of: polyvinylpyrrolidone, copovidone, hydroxypropylmethylcellulose, hydroxypropylcellulose, ethyl cellulose, methylcellulose, or polyethylene oxide. In another aspect described herein, the hygroscopic polymer comprises polyvinylpyrrolidone having a K value from about 70 to about 90. In another aspect described herein, the hygroscopic polymer comprises polyvinylpyrrolidone having a K value from about 10 to about 40. In another aspect described herein, the hygroscopic polymer comprises a mixture of polyvinylpyrrolidone having a K value from about 10 to about 40 and polyvinyl acetate. In another aspect described herein, the hydrophilic polymer comprises at least one of:

polyhydroxylalkylenediamine, dimethylaminoethyl methacrylate copolymer, sodium carboxy methylcellulose, ethylenediamine, sodium alginate, carbomers, poly galacturonic acid, or acrylic methacrylate copolymers. In another aspect described herein, the non-ionic surfactant comprises an HLB value of about 1 to about 25 and a melting point temperature of about 30° C. to about 70° C. In another aspect described herein, the non-ionic surfactant comprises at least one of Pluronic®, Lutrol®, Tween® 80, Span® 80, IGEPAL®, or Triton™ X-100. In another aspect described herein, the active pharmaceutical ingredient comprises at least one of: a 5-aminosalicylic acid drug such as mesalamine, olsalazine, balsalazide or sulfasalazine; a steroid such as prednisone, methylprednisolone, hydrocortisone, cortisol, or budesonide; an immunosuppressant such as azathioprine, 6-mercaptopurine, cyclosporine A, tacrolimus, or methotrexate; a biologic TNF-alpha or integrin inhibitor such as infliximab (Remicade®), adalimumab (Humira®), golimumab (Simponi®), certolizumab (Cimzia®), vedolizumab (Entyvio®), ustekinumab (Stelara®), or natalizumab (Tysabri®), an antibiotic comprising a penicillin, a quinolone such as ciprofloxacin, metronidazole, atropine, diphenoxylate (Lomotil®), dicyclomine (Bentyl®), loperamide (Imodium), rifaximin (Xifaxan®), alosetron (Lotronex®); bile acid binding agents such as cholestyramine (Prevailite®); constipation therapeutics such as linaclotide (Linzess®) or lubiprostone (Amitiza®) fluorouracil (Adrucil®, Efudex® or Fluoroplex®), bevacizumab (Avastin®), irinotecan hydrochloride (Camptosar®), capecitabine (Xeloda®), cetuximab)(Erbitux®), oxaliplatin (Eloxatin®), leucovorin calcium (Wellcovorin®), panitumumab)(Vectibix®), regorafenib (Stivarga®), or aflibercept (Aleya®), or a combination thereof. In another aspect described herein, the active pharmaceutical ingredient comprises mesalamine. In another aspect described herein, the controlled release matrix comprises: (a) oleic acid; (b) a polyethylene glycol glyceride ester; (c) a poloxamer non-ionic surfactant; (d) a mixture of polyvinylpyrrolidone and polyvinyl acetate; (e) a carbomer polymer; (f) dimethylaminoethyl methacrylate copolymer; and (g) an active pharmaceutical ingredient. In another aspect described herein, the controlled release matrix comprises: (a) about 40% to about 55% oleic acid; (b) about 5% to about 20% Gelucire® 43/01; (c) about 1% to about 10% Lutrol® 127U; (d) about 2% to about 8% Kollidon® SR; (e) about 1% to about 6% Carbopol® 971 A; (f) about 2% to about 8% EUDRAGIT® EPO; and (g) about 25% to about 33% of an active pharmaceutical ingredient. In another aspect described herein, the soft capsule shell comprises: (a) a film forming polymer; (b) a plasticizer; (c) a solvent; and (d) optionally, an opacifying agent, a coloring agent, or a pharmaceutical excipient. In another aspect described herein, the soft capsule shell comprises: (a) about 25-50% of at least one film-forming polymer; (b) about 15-25% of at least one plasticizer; (c) about 20-40% of a solvent; (d) optionally, an opacifying agent, a coloring agent, a pharmaceutical excipient, or a combination thereof. In another aspect described herein, the soft capsule shell comprises: (a) about 43% of at least one film-forming polymer; (b) about 20% of at least one plasticizer; (c) about 37% of a solvent; (d) optionally, about 0.7% of an opacifying agent; and (e) optionally, about 0.1% of at least one coloring agent. In another aspect described herein, the soft capsule shell is an enteric soft capsule shell further comprising: (f) an enteric acid insoluble polymer; and (g) an alkali neutralizing agent. In another aspect described herein, the enteric soft capsule shell comprises: (a) about 25-50% of at least one film-forming polymer; (b) about 15-25% of at least one plasticizer; (c) about 20-40% of a solvent; (d) optionally, about 0.7% of an opacifying agent; (e) optionally, about 0.1% of at least one coloring agent; (f) about 8-20% of an enteric acid insoluble polymer; and (g) about 1-5% of an alkali neutralizing agent. In another aspect described herein, the soft capsule shell comprises: gelatin, glycerol, water, titanium oxide, and optionally a coloring agent. In another aspect described herein, the enteric soft capsule shell comprises: gelatin, a methacrylic acid copolymer, glycerol, triethyl citrate, ammonium hydroxide, water, titanium oxide, and optionally a coloring agent.

Another embodiment described herein is a method for manufacturing an oral controlled release controlled release soft capsule shell and matrix comprising: (a) providing a matrix comprising any of the compositions described herein; (b) providing a soft capsule gel mass comprising any of the compositions described herein; (c) casting the soft capsule gel mas into films using heat-controlled drums or surfaces; and (d) forming a soft capsule comprising the matrix composition using rotary die encapsulation technology.

Another embodiment described herein is a soft capsule comprising a controlled release matrix produced by the methods described herein.

Another embodiment described herein is an enteric soft capsule comprising a controlled release matrix produced by the methods described herein.

Another embodiment described herein is a controlled release oral pharmaceutical composition comprising a tamper resistant controlled release matrix comprising: (a) about 40% to about 55% oleic acid; (b) about 5% to about 20% Gelucire® 43/01; (c) about 1% to about 10% Lutrol® 127U; (d) about 2% to about 8% Kollidon® SR; (e) about 1% to about 6% Carbopol® 971 A; (f) about 0.5% to about 8% EUDRAGIT® EPO; and (g) about 25% to about 33% of an active pharmaceutical ingredient; wherein the matrix has controlled release properties; the matrix being encapsulated in an enteric soft capsule shell comprising: (h) about 20-36% gelatin; (i) about 8-20% methacrylic acid copolymer; (j) about 15-22% glycerol and triethyl citrate; (k) about 1-5% ammonia hydroxide; (1) about 20-40% water; and (m) optionally, an opacifying agent, a coloring agent, a pharmaceutical excipient, or combination thereof. In one aspect described herein, the active pharmaceutical ingredient comprises a drug useful for treating inflammatory bowel disease comprising a 5-aminosalicylic acid drug such as mesalamine, olsalazine, balsalazide or sulfasalazine; a steroid such as prednisone, methylprednisolone, hydrocortisone, cortisol, or budesonide; an immunosuppressant such as azathioprine, 6-mercaptopurine, cyclosporine A, tacrolimus, or methotrexate; a biologic TNF-alpha or integrin inhibitor such as infliximab (Remicade®), adalimumab (Humira®), golimumab (Simponi®), certolizumab (Cimzia®), vedolizumab (Entyvio®), ustekinumab (Stelara®), or natalizumab (Tysabri®), an antibiotic comprising a penicillin, a quinolone such as ciprofloxacin, or metronidazole or a combination thereof. In another aspect described herein, the active pharmaceutical ingredient comprises a drug useful for treating irritable bowel syndrome comprising antidiarrheals such as atropine, diphenoxylate (Lomotil®), dicyclomine (Bentyl®), loperamide (Imodium®), rifaximin (Xifaxan®), alosetron (Lotronex®); bile acid binding agents such as cholestyramine (Prevailite®); constipation therapeutics such as linaclotide (Linzess®) or lubiprostone (Amitiza®) or a combination thereof. In another aspect described herein, the active pharmaceutical ingredient comprises a drug useful for treating colon or colorectal cancer comprising fluorouracil (Adrucil®, Efudex® or Fluoroplex®), bevacizumab (Avastin®), irinotecan hydrochloride (Camptosar®), capecitabine (Xeloda®), cetuximab (Erbitux), oxaliplatin (Eloxatin), leucovorin calcium (Wellcovorin®), panitumumab (Vectibix), regorafenib (Stivarga®), or aflibercept (Aleya®), or a combination thereof.

Another embodiment described herein is a method for treating, retarding the progression of, delaying the onset of, prophylaxis of, amelioration of, or reducing the symptoms of a bowel disease comprising inflammatory bowel disease, irritable bowel syndrome, or colon or colorectal cancer in need thereof comprising administering any of the pharmaceutical composition described herein, wherein the active pharmaceutical ingredient is delivered to the colon; and wherein the subject achieves disease remission without substantially experiencing one or more side effects comprising renal impairment, such as interstitial nephritis; headache, gastrointestinal disorders, such as flatulence, cholecystitis, perforated peptic ulcers, gastrointestinal bleeding, colitis, nausea, loss of appetite, hair loss, mouth sores, pancreatitis, rectal polyps, or vomiting; pains, such as abdominal pain, pharyngolaryngeal pain, ear pain, or back pain; abdominal distention, dyspepsia, arthralgia, fatigue, hypertension, tachycardia, abnormal liver function, or skin disorders, such as psoriasis, pyoderma gangrenosum, erythema nodosum, alopecia, pruritus, rash, rash on hands and feet, acne, or urticaria, hepatic impairment such as jaundice, cholestatic jaundice, hepatitis, liver necrosis, or liver failure; hematologic impairment, such as agranulocytosis or aplastic anemia; immune system disorders such as anaphylactic reactions, Stevens-Johnson syndrome (SJS), or drug reactions with eosinophilia and systemic symptoms (DRESS), peripheral neuropathy, Guillain-Barre syndrome, or transverse myelitis or reversible oligospermia or any combination of adverse side effects thereof. In one aspect described herein, the pharmaceutical composition comprises the enteric soft capsule as described herein. Another embodiment described herein is a method for treating, retarding the progression of, delaying the onset of, prophylaxis of, amelioration of, or reducing the symptoms of a bowel disease comprising inflammatory bowel disease, irritable bowel syndrome, or colon or colorectal cancer comprising orally administering to a subject in need thereof any of the pharmaceutical composition described herein, wherein the pharmaceutical composition exhibits an in vitro dissolution rate of less than about 2% to about 20% dissolution at pH 1.2 after about 60 minutes to about 300 minutes; less than about 2% to about 20% dissolution at pH 4.5 after about 60 minutes to about 300 minutes; or at least about a 50% in vitro dissolution rate at pH 7.2 after about 60 minutes to about 480 minutes.

Another embodiment described herein is a method for delivering an active pharmaceutical ingredient to the colon comprising: providing any of the oral pharmaceutical compositions described herein, wherein the composition is resistant to gastric and intestinal fluids at pH 1.2 and pH 4.5 and does not dissolve in the stomach or small intestine and begins dissolving after reaching the colon. In one aspect described herein, the pharmaceutical composition comprises the enteric soft capsule of any of the compositions described herein.

Another embodiment described herein is a kit for dispensing any of the controlled release oral pharmaceutical compositions described herein comprising: (a) at least one soft capsule comprising a controlled release matrix comprising an active pharmaceutical ingredient; (b) at least one receptacle comprising a tamper evident, moisture proof packaging that reduces the ability of removing the oral pharmaceutical composition comprising blister or strip packs, aluminum blister, transparent or opaque polymer blister with pouch, polypropylene tubes, colored blister materials, tubes, bottles, and bottles optionally containing a child-resistant feature, optionally comprising a desiccant, such as a molecular sieve or silica gel; (c) optionally, an insert comprising instructions or prescribing information for the active pharmaceutical ingredient.

DETAILED DESCRIPTION

Figure 1:
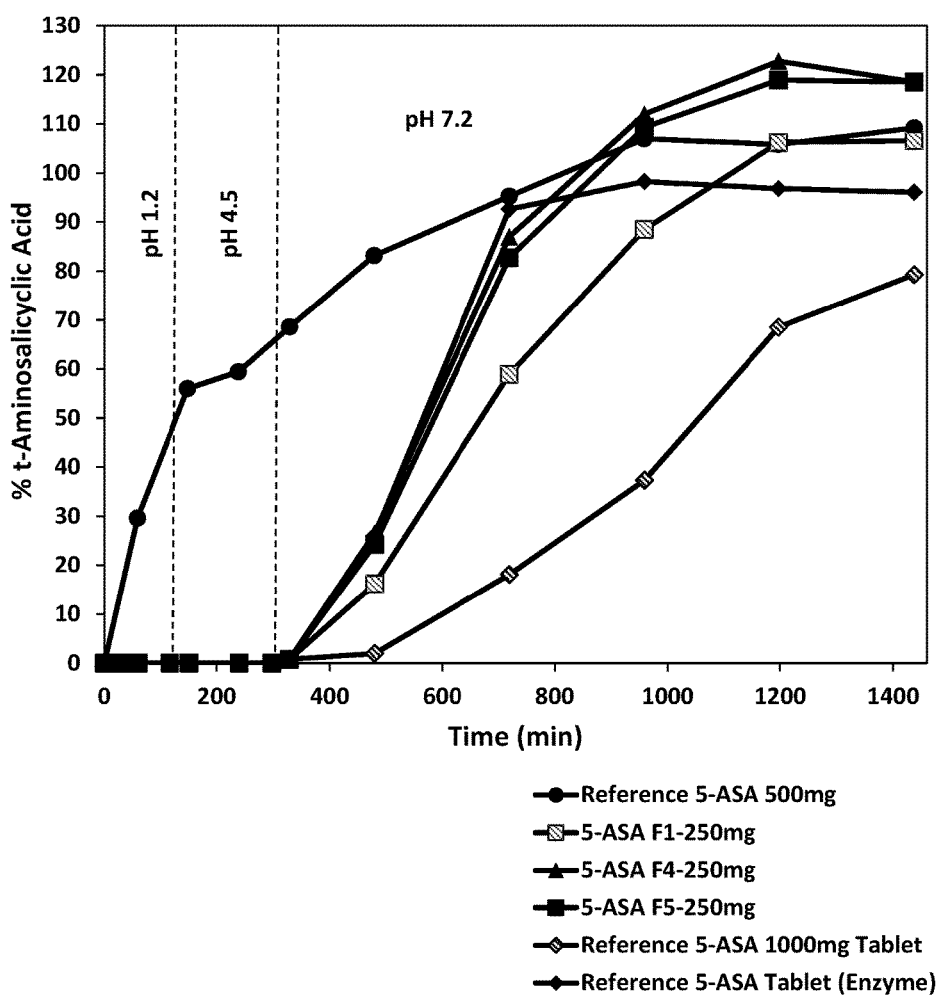
FIG. 1. Release profile of an enteric soft capsule comprising the compositions of Table 7 compared to reference tablets.

Described herein are controlled release pharmaceutical compositions. The pharmaceutical compositions described herein provide controlled release matrices and methods for preparation thereof. Also described herein are compositions and methods for manufacturing soft capsules comprising controlled release pharmaceutical matrices. In some embodiments described herein, the soft capsule is an enteric soft capsule.

The term "active ingredient" or "active pharmaceutical ingredient" or "active pharmaceutical agent" as used herein refers to an agent, active ingredient, compound, or substance, compositions, or mixtures thereof, that provide a pharmacological, often beneficial, effect. Reference to a specific active ingredient includes, where appropriate, the active ingredient and any of its pharmaceutically acceptable salts or esters.

The terms "dosage" or "dose" denote any form of the active ingredient formulation that contains an amount sufficient to produce a therapeutic effect with a single administration. The dosage form used herein is for oral administration. The preferred oral dosage forms are soft capsules or enteric soft capsules.

The terms "active pharmaceutical ingredient load" or "drug load" as used herein refers to the quantity (mass) of the active pharmaceutical ingredient comprised in a single soft capsule fill.

The term "formulation" or "composition" as used herein refers to the active pharmaceutical ingredient or drug in combination with pharmaceutically acceptable excipients. This includes orally administrable formulations as well as formulations administrable by other means.

The term "titration" as used herein refers to the incremental increase in drug dosage to a level that provides the optimal therapeutic effect.

The term "controlled release" as used herein refers to a composition that does not immediately releases an active ingredient. "Controlled release" as used herein encompasses the terms "modified release," "sustained release," "extended release," and "delayed release." In some aspects, the term controlled release further refers to an oral pharmaceutical composition that dissolves in the colon and not the stomach or small intestine and exhibits drug release in the colon. In some other aspects, the term controlled release further refers to an oral pharmaceutical composition that dissolves along the length of the small intestine and not the stomach and exhibits drug release to the and along the length of the small intestine.

The term "delayed release" as used herein refers to a composition that releases an active ingredient according to a desired profile over an extended period under physiological conditions or in an in vitro test. By "extended period" it is meant a continuous period of time of at least about 20 minutes, about 30 minutes, about 1 hour; about 2 hours; about 4 hours; about 6 hours; about 8 hours; about 10 hours; about 12 hours; about 14 hours; about 16 hours; about 18 hours; about 20 hours about 24 hours; or even longer.

The term "modified release" as used herein refers to a composition that releases an active ingredient at a slower rate than does an immediate release formulation under physiological conditions or in an in vitro test.

The term "sustained" release" as used herein refers to a composition that releases an active ingredient over an extended period of time, for example minutes, hours, or days, such that less than all the active ingredient is released initially. A sustained release rate may provide, for example, a release of a certain specified amount of a drug or active ingredient from a dosage form, over a certain period, under physiological conditions or in an in vitro test.

The term "extended release" as used herein refers to a composition that releases an active ingredient over an extended period, such as of at least about 20 minutes, about 30 minutes, about 1 hour; about 2 hours; about 4 hours; about 6 hours; about 8 hours; about 10 hours; about 12 hours; about 14 hours; about 16 hours; about 18 hours; about 20 hours about 24 hours; or even longer; specifically, over a period of at least 18 hours under physiological conditions or in an in vitro assay.

The term "$C_{max}$" as used herein refers to the maximum observed blood (plasma, serum, or whole blood) concentration or the maximum blood concentration calculated or estimated from a concentration to time curve, and is expressed in units of mg/L or ng/mL, as applicable.

The term "$C_{min}$" as used herein refers to the minimum observed blood (plasma, serum, or whole blood) concentration or the minimum blood concentration calculated or estimated from a concentration to time curve, and is expressed in units of mg/L or ng/mL, as applicable.

The term "$C_{avg}$" as used herein refers to the blood (plasma, serum, or whole blood) concentration of the drug within the dosing interval, is calculated as AUC/dosing interval, and is expressed in units of mg/L or ng/mL, as applicable.

The term "$T_{max}$" as used herein refers to the time after administration at which $C_{max}$ occurs, and is expressed in units of hours (h) or minutes (min), as applicable.

The term "$AUC_{0 \to \tau}$" as used herein refers to area under the blood (plasma, serum, or whole blood) concentration versus time curve from time zero to time tau ($\tau$) over a dosing interval at steady state, where tau is the length of the dosing interval, and is expressed in units of h·mg/L or h·ng/mL, as applicable. For example, the term $AUC_{0 \to 12}$ as used herein refers to the area under the concentration versus time curve from 0 to 12 hours.

The term "$AUC_{0 \to \infty}$" as used herein refers to the area under the blood (plasma, serum, or whole blood) concentration versus time curve from time 0 hours to infinity, and is expressed in units of h·mg/L or h·ng/mL, as applicable.

The term "$AUC_{overall}$" as used herein refers to the combined area under the blood (plasma, serum, or whole blood) concentration versus time curve, and is expressed in units of h·mg/L (or h·ng/mL) for at least one or more doses of the pharmaceutical compositions described herein. In one aspect, the "$AUC_{overall}$" refers to the combined area under the blood concentration versus time curve for at least two doses of the pharmaceutical compositions described herein.

The term "treating" refers to administering a therapy in an amount, manner, or mode effective to improve a condition, symptom, or parameter associated with a disorder.

The term "prophylaxis" refers to preventing or reducing the progression of a disorder, either to a statistically significant degree or to a degree detectable to one skilled in the art.

The term "substantially" as used herein means to a great or significant extent, but not completely.

The term "about" as used herein refers to any value that is within a variation of up to ≈10% of the value modified by the term "about."

As used herein, "a" or "an" means one or more unless otherwise specified.

Terms such as "include," "including," "contain," "containing," "has," or "having and the like mean "comprising."

The term "or" can be conjunctive or disjunctive.

Described herein are pharmaceutical compositions comprising controlled release matricis comprising active pharmaceutical ingredients. The matrix and soft capsule shell are structured in such a way to increase delivery of active pharmaceutical ingredients to the colon.

In one embodiment, the pharmaceutical composition described herein comprises a soft capsule comprising a controlled release matrix comprising an active pharmaceutical ingredient. In one aspect, the soft capsule is an enteric soft capsule comprising a controlled release matrix comprising an active pharmaceutical ingredient.

In another embodiment, the soft capsule comprising a matrix can provide controlled release properties. In one aspect, the soft capsule and matrix can be configured to provide controlled release, extended release, sustained release, delayed release, or combinations thereof.

In other embodiments, the pharmaceutical composition described herein comprises controlled release properties. These controlled release properties reduce the likelihood that the active pharmaceutical ingredient can be extracted from the composition through mechanisms, including but not limited to crushing, grating, grinding, cutting of the matrix, to permit solvation or extraction of the active pharmaceutical ingredient. In addition, the controlled release properties reduce the likelihood that the active pharmaceutical ingredient can be extracted from the composition by dissolving or extracting in ethanol solutions of about 1% to about 50%, dissolving in solutions having pH values from about 1 to about 12, or dissolving in household chemical compositions, including water, coffee, vinegar, cola, milk, ethanol, isopropanol, acetone, ethyl acetate, or other common solvents.

In other embodiments described herein, the matrix comprises a lipid or lipophilic vehicle that provides a suspension of the active pharmaceutical ingredient. In one aspect, a soft capsule comprising an active pharmaceutical ingredient provides controlled release of the active pharmaceutical ingredient.

In other embodiments described herein, the pharmaceutical composition provides matrix fills for the active pharmaceutical ingredient, or derivatives thereof, based on lipids or lipophilic materials. The matrices described herein have a hydrophobic (lipophilic) surface in contact with a hydrophilic soft capsule shell to minimize any potential shell-fill interactions, such as when the soft capsules are filled with hydrophilic materials. In one embodiment described herein are methods for manufacturing matrix fills comprising a controlled release matrix comprising an active pharmaceutical ingredient in a soft capsule in the form of a suspension, where part or all of the active pharmaceutical ingredient is suspended within the matrix. In one embodiment described herein is a soft capsule having a shell and a controlled release matrix fill, wherein the matrix includes an active pharmaceutical ingredient suspended as solid particles within the lipophilic vehicle.

In one embodiment described herein, an exemplary controlled release matrix has the composition of Table 1, including all possible iterations of the specified ranges that provide 100% for the total weight percentage, including or excluding the optional colorings, flavorings, or excipients. In another embodiment described herein, the exemplary controlled release matrix may comprise any of the excipients or compositions described in International Patent Application Publication No. WO 2005/009409 and WO 2006/096580, U.S. Patent Application Publication Nos. US 2006/0115527 and US 2007/0053868, and U.S. Pat. Nos. 8,293,270 and 8,333,989, each of which are incorporated by reference herein for such teachings.

TABLE 1

Exemplary Controlled release Matrix Composition

| Component | Exemplary Components | Composition Range (%) |
|---|---|---|
| Lipid or lipophilic vehicle(s) | Liquid lipid vehicle (LLV) and/or Semisolid lipid vehicle (SLV): soybean oil, oleic acid, bee's wax; gelucire | 31-92 (LLV: 25-60/SLV: 6-32) |
| Non-ionic surfactant(s) | Pluronic ® F127, poloxamer, Tween ® 80, Triton ™ X | 1-15 |
| Hygroscopic polymer(s) | Polyvinylpyrrolidone (copovidone), polyvinyl acetate, ethyl cellulose, hydroxypropyl methylcellulose | 1-10 |
| Hydrophilic polymers(s) | Carbopol, Eudragit ®, Ethylenediamine | 2-20 |
| Active pharmaceutical ingredient(s) | Mesalamine | 5-50 |

In another embodiment, the lipid or lipophilic vehicle can be a liquid lipophilic vehicle, a semisolid lipophilic vehicle, or a mixture thereof. Suitable lipid or lipophilic vehicles include mineral oil; light mineral oil; natural oils (e.g., vegetable, corn, canola, sunflower, soybean, olive, coconut, cocoa, peanut, almond, cottonseed, persic, sesame, squalane, castor, cod liver, etc) hydrogenated vegetable oil; partially hydrogenated oils; bee's wax (beeswax); polyethoxylated bee's wax; paraffin; normal waxes; medium chain medium chain monoglycerides, diglycerides and triglycerides; higher aliphatic alcohols; higher aliphatic acids; long chain fatty acids; saturated or unsaturated fatty acids; hydrogenated fatty acids; fatty acid glycerides; polyoxyethylated oleic glycerides; monoglycerides and diglycerides; mono-, bi- or tri-substituted glycerides; glycerol mono-oleate esters; glycerol mono-caprate; glyceryl monocaprylate; propylene glycol dicaprylate; propylene glycol monolaurate; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty alcohols associated with polyethoxylate fatty alcohols; cetyl alcohol; octyl dodecanol; myristyl alcohol; isopropyl myristate, isopropyl palmitate, stearic acid, stearyl alcohol, and others known in the art.

In one embodiment, the lipid or lipophilic vehicle comprises a liquid lipophilic vehicle and a semisolid lipophilic vehicle. In one embodiment, the liquid lipid or lipophilic vehicle can be olive oil, sunflower oil, canola oil, palmitoleic acid, oleic acid, myristoleic acid, linoleic acid, arachidonic acid, paraffin oil, or mineral oil. In another embodiment, the semi-solid lipophilic vehicle can be a polyethylene glycol glyceride ester, paraffin wax, or bees wax. In another embodiment, the semi-solid lipophilic vehicle is Gelucire® 33/01, Gelucire® 37/02, Gelucire® 39/01, Gelucire® 43/01, Gelucire® 44/14, Gelucire® 50/02, Gelucire® 50/13, Gelucire® 53/10, or Gelucire® 62/02. In one aspect, the liquid lipid or lipophilic vehicle is olive oil. In another aspect, the semisolid lipid or lipophilic vehicle comprises a Gelucire®. In another aspect, the semisolid lipid or lipophilic vehicle comprises bee's wax. In one aspect, the Gelucire® semisolid lipid vehicle has a HLB value of about 1 and a melting point of about 43. In one aspect, the semisolid lipid or lipophilic vehicle is Gelucire®43/01.

In another embodiment, the matrix may comprise a polyelectrolyte carrier system. In some aspects, the matrix may comprise multiple polymers with oppositely charged poly ions. Useful polymers for the controlled release matrices described herein are able to undergo neutralization of charged groups in response to changes in pH or additional oppositely charged polymers (e.g., poly acids and poly bases). The changes in ionic strength affect the hydrogen bonding strength and either increase or decrease the strength and interpenetration of the polymer network. In this way, it is possible to increase the specificity and location of the delivery of the active pharmaceutical ingredients described herein along the GI tract and more specifically to the colon. Thus, in some aspects, the use of chemical cross linking agents is avoided, reducing toxicity and side effects. Exemplary polyelectrolytes for use in the controlled release matricis described herein are shown in Table 2.

TABLE 2

Exemplary Natural and Synthetic Polyelectrolytes

| Polymers | Category (based on the charge type) |
| --- | --- |
| Natural Polyelectrolytes | |
| Nucleic acids | Polyanion |
| Poly (L-lysine) | Polycation |
| Poly (L-glutamic acid) | Polyanion |
| Carrageenan | Polyanion |
| Alginates | Polyanion |
| Hyaluronic acid | Polyanion |
| Chemically modified biopolymers | |
| Pectin | Polyanion |
| Chitosan (deacetylation of chitin) | Polycation |
| Cellulose - based | Polyanion or polycation |
| Starch - based | Polyanion or polycation |
| Dextran - based | Polyanion or polycation |
| Synthetic polyelectrolytes | |
| Poly (vinylbenzyl trialkyl ammonium) | Polycation |
| Poly (4-vinyl-N-alkyl-pyridimiun) | Polycation |
| Poly (acryloyl-oxyalkyl-trialkyl ammonium) | Polycation |
| Poly (acryamidoalkyl-trialkyl ammonium) | Polycation |
| Poly (diallydimethyl-ammonium) | Polycation |
| Poly (styrenesulfonic acid) | Polyanion |
| Poly (vinylsulfonic acid0 | Polyanion |
| Poly (acrylic or methacrylic acid) | Polyanion |
| Poly (itaconic acid) | Polyanion |
| Maleic acid/diallylamine copolymer | Polyampholitic |

In one embodiment, the matrix comprises a hydrophilic ionic polymer. In one embodiment, the hydrophilic polymers comprise polyhydroxylalkylenediamine, dimethylaminoethyl methacrylate copolymer, Poly(butyl methacrylate-co-(2-dimethylaminoethyl) methacrylate-co-(2-dimethylaminoethyl) 1:2:1 (Eudragit® EPO); sodium carboxy methylcellulose, carboxymethyl cellulose ethylenediamine, sodium alginate, alginic acid, pectin, carbomers, Carbopol® copolymers (polyacrylic acid polymers), such as Carbopol® 934, Carbopol® 940, Carbopol® 941 or Carbopol® 974P; a Pemulen® polymer; polycarbophil poly galacturonic acid, polyglucoronic acid, chondroitic sulfate, carrageenan, and acrylic methacrylate copolymers. In one aspect, the hydrophilic polymer swells in aqueous media. In another aspect, the hydrophilic polymers swell at a pH of about 4 to about 6. In another embodiment, one or more hydrophilic ionic polymers form ionic interactions. In another embodiment, the matrix comprises anionic polymers, cationic polymers, or mixtures thereof. In another embodiment, a hydrophilic cationic polymer and a hydrophilic anionic polymer are combined to form an ionic polymer complex or network. In one aspect, the hydrophilic ionic polymer is Carbopol® 971A. In another aspect, the hydrophilic ionic polymer is Eudragit® EPO.

In another embodiment, the matrix comprises a polysaccharide ionic polymers. Without being bound by any theory, the use of a polysaccharide network is suitable for selective colonic delivery because of the presence of large amounts of polysaccharidases in the human colon, in addition a plethora of enzyme secreting bacteria. In one aspect, the polysaccharides may be chemically modified to prevent excessive water-based swelling. In another aspect, any enteric polymer described herein can be added to the polysaccharide in the matrix fill.

Exemplary non-limiting polysaccharide ionic polymers useful for the controlled matricis described herein comprise pectin (e.g., calcium and zinc salts of pectin), methoxylated derivatives of pectin, amidated derivatives of pectin, amidated calcium pectinate, chitosan, chitosan derivatives (e.g., methacrylate derivatives of chitosan), amylose, starch (e.g., a mixture of amylose and amylopectin), alginic acid, alginates (e.g., alginate calcium salt), dextran (e.g., dextran esters), fructans (e.g., inulin and methacrylate crosslinked hydrogels), oligofructose, chondroitin sulfate, cellulose, arabinogalactan, arabinoxylan, galactomannan (e.g., guar gum), karaya gum, and xanthan gum or a combination or mixture thereof. In one aspect, the polysaccharide ionic polymers comprise pectin. In another aspect, the polysaccharide ionic polymers comprise calcium and zinc salts of pectin.

In another embodiment, additional fortifying agents may be added to the polysaccharide containing matricis. For example, silk fibroin may be added as an additional agent to reduce or control the swelling of a polysaccharide ionic polymers when in an acqueous environment. International Patent Application Publication Nos. WO 2014/152097 and WO 1997/08315 and U.S. Pat. Nos. 5,245,012 and 8,206,774 are each incorporated by reference herein for their specific teachings of silk polymers and modified silk polymers thereof.

In one embodiment, the matrix comprises a non-ionic surfactant. The surfactant can have a hydrophilic/lipophilic balance (HLB) value between about 1 and about 25 and a melting point between about 25° C. and about 70° C. The HLB characteristic of surfactants can be determined in accordance with "Physical Pharmacy: Physical Chemical Principles in the Pharmaceutical Sciences," Fourth Edition, pp. 371-373, A. Martin, Ed., Lippincott Williams & Wilkins, Philadelphia (1993). Suitable non-ionic surfactants include: Pluronic® 10R5, Pluronic® 17R2, Pluronic® 17R4, Pluronic® 25R2, Pluronic® 25R4, Pluronic® 31R1, Pluronic® F 108, Pluronic® F 108 NF, Pluronic® F 108, Pluronic® F 108NF, Poloxamer 338, Pluronic® F 127, Pluronic® F 127 NF, Pluronic® F 127 NF 500 BHT Prill, Pluronic® F 127 NF Prill, Poloxamer 407, Pluronic® F 38, Pluronic® F 38 Pastille, Pluronic® F 68, Pluronic® F 68 LF Pastille, Pluronic® F 68 NF, Pluronic® F 68 NF Prill, Poloxamer 188, Pluronic® F 68 Pastille, Pluronic® F 77, Pluronic® F 77 Micropastille, Pluronic® F 87, Pluronic® F 87 NF, Pluronic® F 87 NF Prill, Poloxamer 237, Pluronic® F 88, Pluronic® F 88 Pastille, Pluronic® F 98, Pluronic® L 10, Pluronic® L 101, Pluronic® L 121, Pluronic® L 31, Pluronic® L 35, Pluronic® L 43, Pluronic® L 61, Pluronic® L 62, Pluronic® L 62 LF, Pluronic® L 62D, Pluronic® L 64, Pluronic® L 81, Pluronic® L 92, Pluronic® N 3, Pluronic® P 103, Pluronic® P 104, Pluronic® P 105, Pluronic® P 123 Surfactant, Pluronic® P 65, Pluronic® P 84, Pluronic® P 85, Adogen® 464, Alkanol® 6112, Brij® 52, Brij® 93, Brij® S2, Brij® S, Brij® 58, Brij® C10, Brij® L4, Brij® O10, Brij® O10, BRIJ® 020, Brij® S10, Brij® S20, ethylenediamine tetrakis(ethoxylate-block-propoxylate) tetrol, ethylenediamine tetrakis(ethoxylate-block-propoxylate) tetrol, ethylenediamine tetrakis(propoxylate-block-ethoxylate) tetrol, IGEPAL® CA-210, IGEPAL® CA-520, IGEPAL® CA-720, IGEPAL® CO-520, IGEPAL® CO-630, IGEPAL® CO-720, IGEPAL® CO-890, IGEPAL® DM-970, MERPOL® DA, MERPOL® HCS, MERPOL® OJ, MERPOL® SE, MERPOL® SH, MERPOL® A, Poly (ethylene glycol) sorbitan tetraoleate, poly(ethylene glycol) sorbitol hexaoleate, poly(ethylene glycol) (12), poly(ethylene glycol) (18), polyethylene-block-poly(ethylene glycol), sorbitan monopalmitate, 2,4,7,9-tetramethyl-5-decyne-4,7-diol ethoxylate, Nonidet™ P-40, Triton™ N-101, Triton™ X-100, Triton™ X-114, Triton™ X-405, TWEEN® 20, TWEEN® 40, TWEEN® 60, TWEEN® 85, Zonyl®FS-300, or Zonyl® FSN. In one embodiment, the non-ionic surfactant comprises Pluronic® F127, Tween® 80, Span® 80, IGEPAL®, or Triton™ X-100. In one aspect, the non-ionic surfactant comprises a poloxamer. In one aspect, the non-ionic surfactant comprises Pluronic® F 127.

In another embodiment, the matrix comprises a hygroscopic polymer. In one embodiment, the hygroscopic polymers include polyvinylpyrrolidone, copovidone, hydroxypropylmethylcellulose, hydroxypropylcellulose, ethyl cellulose, methylcellulose, and polyethylene oxide. Polyvinylpyrrolidone may have a K value of about 10 to about 100. Suitable hygroscopic polymers include polyvinyl alcohol, a copolymer of polyvinylpyrrolidone and polyvinyl acetate, hydroxypropyl cellulose, hydroxypropyl methylcellulose, hydroxyethyl cellulose, hydroxymethyl cellulose, gelatin, polyethylene oxide, such as POLYOX™ 100,000-600,000 MW, acacia, dextrin, starch, polyhydroxyethylmethacrylate, a water-soluble non-ionic polymethacrylate or copolymer thereof, a modified cellulose, a modified polysaccharide, a non-ionic gum, or a non-ionic polysaccharide. In one aspect, the hygroscopic polymer is polyvinylpyrrolidone. In one aspect, the hygroscopic polymer is a mixture of polyvinylpyrrolidone and polyvinyl acetate. In one aspect the hygroscopic polymer comprises Kollidon® SR (i.e., a mixture of about 80% polyvinyl acetate and 19% polyvinylpyrrolidone K30. In one aspect, the hygroscopic polymer comprises Kollidon® 90 F (i.e., polyvinylpyrrolidone K90). In one aspect, the hygroscopic polymer comprises a cellulose polymer. In one aspect, the hygroscopic polymer comprises hydroxypropylmethylcellulose (e.g., HPMC 4M). In another aspect, the hygroscopic polymer is a polyethylene oxide polymer (e.g., POLYOX™ 100,000).

In another embodiment, the matrix comprises a pH buffering agent. Suitable pharmaceutically acceptable buffering agents comprise arginine, aminomethyl propanol, tetrahydroxypropyl ethylenediamine, triethanolamine, tromethamine, PEG-15 cocamine, di-isopropanol amine, tri-isopropanol amine, N-methyl-D-glucamine, glycine, malate, tartarate, lactate, citrate, acetate, sodium bicarbonate, sodium phosphate, or other buffering agents, having pKas at any physiologically acceptable pH, generally from about pH 4 to about pH 7. Amino acids or other physiological metabolites may be used as buffering agents. A combination of buffering agents may also be employed, such as phosphate and acetate, and the like. In one aspect, the pH buffering agent is N-methyl-D-glucamine (e.g., meglumine).

In another embodiment, the matrix comprises a neutralizing agent. Suitable pharmaceutically acceptable neutralizing agents comprise HCl, phosphoric acid, carbonic acid, sodium hydroxide, ammonium hydroxide, potassium hydroxide, sodium bicarbonate, sodium carbonate, and the like.

In another embodiment, the matrix can include a hydrophilic internal phase and a lipid or lipophilic external phase. The internal phase can also be structured. A "structured" internal phase, as used herein, means a solid, semisolid, or a gel whose shape is relatively stable and does not usually aggregate to form a large globule. A structured internal phase therefore provides controlled drug release and stabilizes the physical state of the matrix. Without being bound to any theory, it is believed that the structured nature of the matrix impedes solvation and/or diffusion of the active pharmaceutical ingredient out of the matrix.

In another embodiment, the active pharmaceutical ingredient can be dispersed in the internal phase as a suspension form. In another embodiment, the active pharmaceutical ingredient can be dispersed in the internal phase as a solid form.

In one embodiment described herein, the matrix may comprise one or more lipid or lipophilic vehicles, one or more hydrophilic polymers, one or more hygroscopic polymers, optionally, one or more non-ionic surfactants, optionally, one or more pH buffering agent, and one or more active pharmaceutical ingredients. Without being bound to any theory, it is believed that the hydrophilic cationic and anionic polymers described herein combine within the matrix to form polymer networks or complexes comprising ionic interactions. Further, without being bound to any theory, it is believed that the ionic polymer network swells when hydrated with an aqueous solution and the swelling impedes the dissolution and/or diffusion of the active pharmaceutical ingredient out of the matrix. Without being bound by any theory, it is believed that non-ionic surfactants and hygroscopic polymers facilitate hydration of the hydrophilic ionic polymers described herein. Moreover, without being bound to any theory, the lipid or lipophilic vehicle of the matrix further prevents diffusion and/or solvation of the active pharmaceutical ingredient. Without being bound to any theory, it is believed that the suspension agents prevent precipitation of the active pharmaceutical ingredient or other matrix components. The matrix compositions described herein provide for a controlled release profile for the delivery of active pharmaceutical ingredients to and along the length of the small intestine and not the stomach after ingestion by a subject. The matrix compositions described herein further provide for a controlled release profile for the delivery of active pharmaceutical ingredients selectively to or along the length of the colon and not the stomach or small intestine after ingestion by a subject.

In another embodiment, the lipid or lipophilic vehicle comprises a liquid lipid or lipophilic vehicle, a semisolid lipid or lipophilic vehicle, or a combination thereof. In one embodiment, the total lipid or lipophilic vehicle comprises one or more liquid lipid vehicles and one or more semi-solid lipid vehicles. In one embodiment, the total lipid or lipophilic vehicle comprises about 30% to about 92% of the total matrix mass, including all integers within the specified range. The total lipid or lipophilic vehicle comprises about 30%, about 35%, about 40%, about 45%, about 50%, about 55%, about 60%, about 65%, about 70%, about 75%, about 80%, about 85%, or about 90% of the total matrix mass. In one embodiment, the total lipid or lipophilic vehicle comprises about 40% to about 55% of the total matrix mass, including all integers within the specified range. In one embodiment, the total lipid or lipophilic vehicle comprises about 50% to about 55% of the total matrix mass, including all integers within the specified range. In one aspect, the total lipid or lipophilic vehicle comprises about 55% of the total matrix mass. In another aspect, the total lipid or lipophilic vehicle comprises about 53% of the total matrix mass. In another aspect, the total lipid or lipophilic vehicle comprises about 50% of the total matrix mass. In another aspect, the total lipid or lipophilic vehicle comprises about 49% of the total matrix mass. In another aspect, the total lipid or lipophilic vehicle comprises about 49% of the total matrix mass. In another aspect, the total lipid or lipophilic vehicle comprises about 44% of the total matrix mass.

In another embodiment, one or more liquid lipid or lipophilic vehicles comprise from about 25% to about 60% of the total matrix mass, including all integers within the specified range. The one or more lipid or lipophilic vehicles comprise about 25%, about 30%, about 32%, about 34%, about 36%, about 38%, about 40%, about 42%, about 45%, about 50%, about 55%, or about 60% of the total matrix mass. In one embodiment, the total liquid lipid or lipophilic vehicle comprises from about 38% to about 52% of the total matrix mass, including all integers within the specified range. In one aspect, the total liquid lipid or lipophilic vehicle comprises about 38% of the total matrix mass. In one aspect, the total liquid lipid or lipophilic vehicle comprises about 46% of the total matrix mass. In one aspect, the total liquid lipid or lipophilic vehicle comprises about 50% of the total matrix mass.

In another embodiment, one or more semisolid lipid or lipophilic vehicles comprise from about 4% to about 32% of the total matrix mass, including all integers within the specified range. The one or more semisolid lipid or lipophilic vehicles comprise about 4%, about 5%, about 6%, about 7%, about 8%, about 9%, about 10%, about 12%, about 15%, about 18%, about 20%, about 22%, about 25%, about 28%, about 30%, or about 32% of the total matrix mass. In one embodiment, the total semisolid lipid or lipophilic vehicle comprises from about 4% to about 15% of the total matrix mass including all integers within the specified range. In one aspect, the total semisolid lipid or lipophilic vehicle comprises about 16% of the total matrix mass. In one aspect, the total semisolid lipid or lipophilic vehicle comprises about 14% of the total matrix mass. In one aspect, the total semisolid lipid or lipophilic vehicle comprises about 12% of the total matrix mass. In one aspect, the total semisolid lipid or lipophilic vehicle comprises about 8% of the total matrix mass. In one aspect, the total semisolid lipid or lipophilic vehicle comprises about 6% of the total matrix mass. In one aspect, the total semisolid lipid or lipophilic vehicle comprises about 4% of the total matrix mass.

In another embodiment, the ratio of the liquid lipid vehicle to semisolid lipid ranges from about 2:1 to about 14:1, including all iterations of ratios within the specified range. In one embodiment, the ratio of the lipid liquid to semisolid liquid ranges from about 2.5:1 to about 13:1, including all iterations of ratios within the specified range. In one aspect, the ratio of the lipid liquid to semisolid liquid is about 13:1. In one aspect, the ratio of the lipid liquid to semisolid liquid is about 10:1. In one aspect, the ratio of the lipid liquid to semisolid liquid is about 8:1. In one aspect, the ratio of the lipid liquid to semisolid liquid is about 7:1. In one aspect, the ratio of the lipid liquid to semisolid liquid is about 6:1. In one aspect, the ratio of the lipid liquid to semisolid liquid is about 5:1. In one aspect, the ratio of the lipid liquid to semisolid liquid is about 4:1. In one aspect, the ratio of the lipid liquid to semisolid liquid is about 3:1. In one aspect, the ratio of the lipid liquid to semisolid liquid is about 2:1.

In another embodiment, the one or more hygroscopic polymers comprise from about 1% to about 25% of the total matrix mass, including all integers within the specified range. The one or more hygroscopic polymers comprise about 1%, about 2%, about 3%, about 4%, about 5%, about 6%, about 7%, about 8%, about 9%, about 10%, about 12%, about 15%, about 18%, about 20%, about 22%, or about 25% of the total matrix mass. In another embodiment, the total hygroscopic polymer content comprises from about 5% to about 18% of the total matrix mass, including all integers within the specified range. In another embodiment, the total hygroscopic polymer content comprises from about 10% to about 16% of the total matrix mass, including all integers within the specified range. In one aspect, the total hygroscopic polymer content comprises about 20% of the total matrix mass. In one aspect, the total hygroscopic polymer content comprises about 18% of the total matrix mass. In one aspect, the total hygroscopic polymer content comprises about 16% of the total matrix mass. In one aspect, the total hygroscopic polymer content comprises about 15% of the total matrix mass. In one aspect, the total hygroscopic polymer content comprises about 13% of the total matrix mass. In one aspect, the total hygroscopic polymer content comprises about 12% of the total matrix mass. In one aspect, the total hygroscopic polymer content comprises about 11% of the total matrix mass. In one aspect, the total hygroscopic polymer content comprises about 10% of the total matrix mass. In one aspect, a hygroscopic polymer comprises about 9% of the total matrix mass. In one aspect, a hygroscopic polymer comprises about 8% of the total matrix mass. In one aspect, a hygroscopic polymer comprises about 7% of the total matrix mass. In one aspect, a hygroscopic polymer comprises about 6% of the total matrix mass. In one aspect, a hygroscopic polymer comprises about 5% of the total matrix mass. In one aspect, a hygroscopic polymer comprises about 4% of the total matrix mass. In one aspect, a hygroscopic polymer comprises about 3% of the total matrix mass. In one aspect, a hygroscopic polymer comprises about 2% of the total matrix mass.

In another embodiment, the matrix comprises a non-ionic surfactant. In another embodiment, the non-ionic surfactant comprises from about 1% to about 15% of the total matrix mass, including all integers within the specified range. In another embodiment, non-ionic surfactant comprises from about 2.5% to about 10% of the total matrix mass, including all integers within the specified range. In one aspect, non-ionic surfactant comprises about 2.5% of the total matrix mass. In one aspect, non-ionic surfactant comprises about 4% of the total matrix mass. In one aspect, the non-ionic surfactant comprises about 6.5% of the total matrix mass. In one aspect, the non-ionic surfactant comprises about 7% of the total matrix mass. In one aspect, the non-ionic surfactant comprises about 8.5% of the total matrix mass.

In another embodiment, the total amount of hygroscopic polymer and non-ionic surfactant ranges from about 4% to about 20% of the total matrix mass, including all integers within the specified range. In one aspect, the total amount of hygroscopic polymer and non-ionic surfactant comprises about 6% of the total matrix mass. In one aspect, the total amount of hygroscopic polymer and non-ionic surfactant comprises about 10% of the total matrix mass. In one aspect, the total amount of hygroscopic polymer and non-ionic surfactant comprises about 18% of the total matrix mass.

In another embodiment, the ratio of the non-ionic surfactant to the hygroscopic polymer ranges from about 0.2:1 to about 15:1, including all iterations of ratios within the specified range. In another embodiment, the ratio of the non-ionic surfactant to the hygroscopic polymer ranges from about 0.2:1 to about 5:1, including all iterations of ratios within the specified range. In one aspect, the ratio of the non-ionic surfactant to the hygroscopic polymer is about 0.7:1. In one aspect, the ratio of the non-ionic surfactant to the hygroscopic polymer is about 1.5:1. In one aspect, the ratio of the non-ionic surfactant to the hygroscopic polymer is about 2:1. In one aspect, the ratio of the non-ionic surfactant to the hygroscopic polymer is about 3.5:1.

In another embodiment, the ratio of lipophilic vehicle to the hygroscopic polymer and non-ionic surfactant ranges from about 2:1 to about 85:1, including all iterations of ratios within the specified range. In another embodiment, the ratio of lipophilic vehicle to the hygroscopic polymer and non-ionic surfactant ranges from about 2:1 to about 20:1, including all iterations of ratios within the specified range. In another embodiment, the ratio of lipophilic vehicle to the hygroscopic polymer and non-ionic surfactant ranges from about 2:1 to about 10:1, including all iterations of ratios within the specified range. In one aspect, the ratio of the lipophilic vehicle to the hygroscopic polymer and non-ionic surfactant is about 3:1. In one aspect, the ratio of the lipophilic vehicle to the hygroscopic polymer and non-ionic surfactant is 3.4:1. In one aspect, the ratio of the lipophilic vehicle to the hygroscopic polymer and non-ionic surfactant is about 4:1. In one aspect, the ratio of the lipophilic vehicle to the hygroscopic polymer and non-ionic surfactant is 4.2:1. In one aspect, the ratio of the lipophilic vehicle to the hygroscopic polymer and non-ionic surfactant is 12:1. In one aspect, the ratio of the lipophilic vehicle to the hygroscopic polymer and non-ionic surfactant is 30:1.

In another embodiment, the matrix comprises a hydrophilic polymer. In one aspect, the hydrophilic polymer is a non-ionic polymer, an anionic polymer, a cationic polymer, or a combination thereof. In one aspect, the matrix comprises a hydrophilic anionic polymer. In another aspect, the matrix comprises a hydrophilic cationic polymer. In another aspect, the matrix comprises a hydrophilic anionic polymer and hydrophilic cationic polymer.

In another embodiment, the hydrophilic polymer comprises from about 2% to about 20% of the total matrix mass, including all integers within the specified range. The hydrophilic polymer comprises about 2%, about 3%, about 4%, about 5%, about 6%, about 7%, about 8%, about 9%, about 10%, about 12%, about 15%, about 18%, or about 20% of the total matrix mass. In one aspect, the hydrophilic polymer comprises about 10% of the total matrix mass. In one aspect, the hydrophilic polymer comprises about 9% of the total matrix mass. In one aspect, the hydrophilic polymer comprises about 8% of the total matrix mass. In one aspect, the hydrophilic polymer comprises about 7% of the total matrix mass. In one aspect, the hydrophilic polymer comprises about 6% of the total matrix mass. In one aspect, the hydrophilic polymer comprises about 5% of the total matrix mass. In one aspect, the hydrophilic polymer comprises about 4% of the total matrix mass. In one aspect, the hydrophilic polymer comprises about 3% of the total matrix mass. In one aspect, the hydrophilic polymer comprises about 2% of the total matrix mass. In one aspect, the hydrophilic polymer comprises about 1% of the total matrix mass.

In one embodiment, the matrix comprises multiple species of hydrophilic ionic polymers. In another embodiment, the matrix comprises two species of hydrophilic ionic polymers. In one embodiment, one species of hydrophilic polymer is one or more anionic polymers and the other species of hydrophilic polymer is one or more cationic polymers. In one embodiment, the ratio of one species of hydrophilic ionic polymer to a second hydrophilic ionic polymer is about 0.3:1 to about 5:1, including all iterations of ratios within the specified range. In one aspect, the ratio of one species of hydrophilic ionic polymer to a second hydrophilic ionic polymer is about 0.8:1. In one aspect, the ratio of one species of hydrophilic ionic polymer to a second hydrophilic polymer ionic is about 0.7:1. In one aspect, the ratio of one species of hydrophilic ionic polymer to a second hydrophilic polymer ionic is about 0.5:1. In one aspect, the ratio of one species of hydrophilic ionic polymer to a second hydrophilic polymer ionic is about 0.4:1. In one aspect, the ratio of one species of hydrophilic ionic polymer to a second hydrophilic polymer ionic is about 0.3:1. In one aspect, one hydrophilic polymer species is anionic, and the other hydrophilic polymer species is cationic.

In another embodiment, the matrix comprises a pH buffering agent. In one aspect, the pH buffering agent comprises a pKa from about pH 2.5 to about pH 12, including all integers within the specified range. In another aspect, the pH buffering agent comprises a pKa from about pH 5 to about pH 11. In another aspect, the pH buffering agent has a pKa of about 7.5 to about 10, including all integers within the specified range. In one aspect, the pH buffering agent has a pKa of about 9.

In one embodiment, the pH buffering agent comprises about 1% to about 8% of the total matrix mass, including all integers within the specified range. In one aspect, the pH buffering agent comprises about 2% of the total matrix mass. In one aspect, the pH buffering agent comprises about 4% of the total matrix mass. In one aspect, the pH buffering agent comprises about 5.5% of the total matrix mass.

In some embodiments, the ratio of the pH buffering agent to the ionic hydrophilic polymers is from about 0.2:1 to about 3:1, including all iterations of ratios within the specified range. In some embodiments, the ratio of the pH buffering agent to the ionic hydrophilic polymers is from about 0.2:1 to about 0.5:1, including all iterations of ratios within the specified range. In one aspect, the ratio of the pH buffering agent to the ionic hydrophilic polymers is about 0.3. In one aspect, the ratio of the pH buffering agent to the ionic hydrophilic polymers is about 0.5.

The total hydrophilic composition of the matrix comprises one or more one or more hygroscopic polymers; one or more hydrophilic polymers; optionally, one or more non-ionic surfactants, and optionally, one or more pH buffering agents. In one embodiment, the total hydrophilic composition of the matrix comprises about 7% to about 48% of the total matrix mass, including all integers within the specified range. In another embodiment, the total hydrophilic matrix composition comprises about 18% to about 32% of the total matrix mass, including all integers within the specified range. In one embodiment, the total hydrophilic matrix composition comprises about 18% to about 22% of the total matrix mass, including all integers within the specified range. In one aspect, the total hydrophilic matrix composition comprises about 7% of the total matrix mass. In one aspect, the total hydrophilic matrix composition comprises about 10% of the total matrix mass. In one aspect, the total hydrophilic matrix composition comprises about 14% of the total matrix mass. In one aspect, the total hydrophilic matrix composition comprises about 14% of the total matrix mass. In one aspect, the total hydrophilic matrix composition comprises about 18% of the total matrix mass. In one aspect, the total hydrophilic matrix composition comprises about 19% of the total matrix mass. In one aspect, the total hydrophilic matrix composition comprises about 20% of the total matrix mass. In one aspect, the total hydrophilic matrix composition comprises about 21% of the total matrix mass. In one aspect, the total hydrophilic matrix composition comprises about 22% of the total matrix mass.

In another embodiment, the ratio of the total lipid or lipophilic vehicle to the total hydrophilic matrix composition is from about 1:1 to about 13:1, including all iterations of ratios within the specified range. In another embodiment, the ratio of the lipid or lipophilic vehicle to the hydrophilic matrix composition is from about 1:1 to about 3:1, including all iterations of ratios within the specified range. In one aspect, the ratio of the lipid or lipophilic vehicle to the hydrophilic matrix composition is about 1.5:1. In one aspect, the ratio of the lipid or lipophilic vehicle to the hydrophilic matrix composition is about 2.5:1. In one aspect, the ratio of the lipid or lipophilic vehicle to the hydrophilic matrix composition is about 2.3:1. In one aspect, the ratio of the lipid or lipophilic vehicle to the hydrophilic matrix composition is about 2.7:1. In one aspect, the ratio of the lipid or lipophilic vehicle to the hydrophilic matrix composition is about 4:1. In one aspect, the ratio of the lipid or lipophilic vehicle to the hydrophilic matrix composition is about 4.5:1. In one aspect, the ratio of the lipid or lipophilic vehicle to the hydrophilic matrix composition is about 8:1.

In another embodiment, the matrix comprises a suspension agent. In one embodiment, the suspension agent comprises about 0.5% to about 5% of the total matrix mass, including all integers within the specified range. In one embodiment, the suspension agent comprises about 0.8% to about 2% of the total matrix mass, including all integers within the specified range. In one aspect, the suspension agent comprises about 2% of the total matrix mass. In another aspect, the suspension agent comprises about 1.5% of the total matrix mass. In another aspect, the suspension agent comprises about 1.3% of the total matrix mass. In another aspect, the suspension agent comprises about 1.2% of the total matrix mass. In one aspect, the suspension agent comprises about 1.2% of the total matrix mass. In one aspect, the suspension agent comprises about 1% of the total matrix mass. In one aspect, the suspension agent comprises about 0.9% of the total matrix mass. In one aspect, the suspension agent comprises about 0.8% of the total matrix mass.

In one embodiment, the matrix comprises a lipid or lipophilic composition and hydrophilic composition. In one embodiment, the lipid or lipophilic composition comprises one or more liquid lipid vehicles and one or more semi-solid lipid vehicles and the hydrophilic composition comprises one or more hygroscopic polymers, one or more hydrophilic polymers. In another embodiment, the hydrophilic matrix composition comprises. In one embodiment, the matrix further comprises a suspension agent. In another embodiment, the matrix further comprises a non-ionic surfactant. In another embodiment, the matrix further comprises a pH buffering agent.

In one embodiment, the matrix comprises one or more liquid lipid vehicles, one or more semi-solid lipid vehicles, one or more one or more hygroscopic polymers, one or more hydrophilic polymers, one or more non-ionic surfactants, one or more pH buffering agents, and one or more active pharmaceutical ingredients. In one embodiment, the matrix comprises any one of the compositions of Tables 7-11

In one embodiment, the matrix comprises one or more liquid lipid vehicles, one or more semi-solid lipid vehicles, one or more one or more hygroscopic polymers, one or more hydrophilic polymers, one or more suspension agents, and one or more active pharmaceutical ingredients. In one embodiment, the matrix comprises any one of the compositions of Tables 7-11.

In another embodiment, the one or more active pharmaceutical ingredient comprises from about 1% to about 50% of the total matrix mass, including all integers within the specified range. In another embodiment, the active pharmaceutical ingredient comprises from about 5% to about 30% of the total matrix mass, including all integers within the specified range. In one aspect, the active pharmaceutical ingredient comprises about 5% of the total matrix mass. In one aspect, the active pharmaceutical ingredient comprises about 10% of the total matrix mass. In one aspect, the active pharmaceutical ingredient comprises about 15% of the total matrix mass. In one aspect, the active pharmaceutical ingredient comprises about 20% of the total matrix mass. In one aspect, the active pharmaceutical ingredient comprises about 25% of the total matrix mass. In one aspect, the active pharmaceutical ingredient comprises about 33% of the total matrix mass.

In another embodiment, the ratio of the active pharmaceutical ingredient to the total hydrophilic composition of the matrix ranges from about 0.1:1 to about 5.6:1, including all iterations of ratios within the specified range. In another embodiment, the ratio of the active pharmaceutical ingredient to the total hydrophilic composition of the matrix ranges from about 0.1:1 to about 2.6:1, including all iterations of ratios within the specified range. The ratio of the active pharmaceutical ingredient to the total hydrophilic composition of the matrix can be 0.1:1, 0.3:1, 0.5:1, 1:1, 1.1:1, 1.2:1, 1.3:1, 1.4:1, 1.7:1, 1.8:1, 2:1, 2.4:1, 2.6:1, 3:1, 4:1, or 5:1. In one aspect, the ratio of the active pharmaceutical ingredient to the total hydrophilic composition of the matrix is about 4.5:1. In one aspect, the ratio of the active pharmaceutical ingredient to the total hydrophilic composition of the matrix is about 1.8:1. In one aspect, the ratio of the active pharmaceutical ingredient to the total hydrophilic composition of the matrix is about 1.7:1. In one aspect, the ratio of the active pharmaceutical ingredient to the total hydrophilic composition of the matrix t is about 1.6:1. In one aspect, the ratio of the active pharmaceutical ingredient to the total hydrophilic composition of the matrix is about 1.4:1. In one aspect, the ratio of the active pharmaceutical ingredient to the total hydrophilic composition of the matrix is about 1.2:1. In one aspect, the ratio of the active pharmaceutical ingredient to the total hydrophilic composition of the matrix is about 0.5:1.

In another embodiment, the ratio of the active pharmaceutical ingredient to the total lipid or lipophilic composition of the matrix ranges from about 0.2:1 to about 1.8:1, including all iterations of ratios within the specified range. The ratio of the active pharmaceutical ingredient to the total lipid or lipophilic composition of the matrix can be 0.1:1, 0.2:1, 0.5:1, 0.6:1, 0.8:1, 0.9:1, 1:1, 1.2:1, 1.4:1, or 1.8:1. In one aspect, the ratio of the active pharmaceutical ingredient to the total lipid or lipophilic composition of the matrix is about 1.4:1. In one aspect, the ratio of the active pharmaceutical ingredient to the total lipid or lipophilic composition of the matrix is about 1:1. In one aspect, the ratio of the active pharmaceutical ingredient to the total lipid or lipophilic composition of the matrix t is about 0.8:1. In one aspect, the ratio of the active pharmaceutical ingredient to the total lipid or lipophilic composition of the matrix is about 0.6:1. In one aspect, the ratio of the active pharmaceutical ingredient to the total lipid or lipophilic composition of the matrix is about 0.5:1.

In another embodiment, the ratio of the active pharmaceutical ingredient to the total matrix composition ranges from about 0.1:1 to about 1:1, including all iterations of ratios within the specified range. The ratio of the active pharmaceutical ingredient to the total matrix composition can be 0.1:1, 0.2:1, 0.3:1, 0.4:1, 0.5:1, 0.6:1, 0.7:1, 0.8:1, 0.9:1, or 1:1. In another embodiment, the ratio of the active pharmaceutical ingredient to the total matrix composition ranges from about 0.2:1 to about 0.5:1, including all iterations of ratios within the specified range. In another embodiment, the ratio of the active pharmaceutical ingredient to the total matrix composition ranges from about 0.2:1 to about 0.4:1, including all iterations of ratios within the specified range. In one aspect, the ratio of the active pharmaceutical ingredient to the total matrix composition is about 0.3:1. In one aspect, the ratio of the active pharmaceutical ingredient to the total matrix composition is about 0.4:1. In one aspect, the ratio of the active pharmaceutical ingredient to the total matrix composition is about 0.5:1.

In one embodiment, the matrix contains an active pharmaceutical ingredient or therapeutic agent in a suspended, form, soluble form, insoluble form, or combinations thereof. The active pharmaceutical ingredient or therapeutic agent may be appropriately selected for treating, ameliorating the symptoms of, or delaying the onset of a medical condition or disease. Non-limiting examples of active pharmaceutical ingredients or therapeutic agents include a peptide pharmaceutical prone to be degraded in the stomach and/or small intestine, a therapeutic agent for diabetes mellitus, a therapeutic agent for osteoporosis, a therapeutic agent for the treatment of neurodegenerating diseases, a therapeutic agent for the treatment of endometriosis, a promoting agent for uterine contraction and/or labor, an ovulation inducing drug, a therapeutic agent for acromegaly, an agent for somatotropin substitution therapy, a therapeutic agent for treating diabetes insipidus, a therapeutic agent for treating colorectal cancer, a Lactobacillus pharmaceutical preparation, a therapeutic agent for treating autoimmune diseases, a therapeutic agent for treating a bowel disease, such as a therapeutic agent for treating irritable bowel syndrome, or inflammatory bowel syndrome, such as Crohn's disease, ulcerative colitis, or irritable colon syndrome; an antitumor agent, antibiotics, anti-inflammatory agents, chemotherapeutic agents, immunosuppressants, steroids, vitamins, laxatives, and polynucleotides (gene pharmaceutical such as a ribozyme, antisense oligonucleotides, RNAi, an aptamer or the like) or a mixture of active pharmaceutical ingredients and therapeutic agents useful for treating any or all of the conditions described herein.

Non-limiting active pharmaceutical ingredients useful for the controlled release matricis described herein comprise human insulin, peptide with human insulin-like action, thyroid hormone (PTH), peptide with PTH-like action, human calcitonin, peptide with human calcitonin-like action, thyrotropin releasing hormone (TRH), taltirelin hydrate, luteinizing hormone-releasing hormone (LH-RH), goserelin acetate, buserelin acetate, nafarelin acetate, oxytocin, human hypophyseal gonadotropin, octreotide acetate, somatropin, human chorionic gonadotropin, desmopressin acetate, 5-fluorouracil, bleomycin, doxifluridine, tegafur, tegafur 5-aminosalicylic acid, salazosulfapyridine, infliximab, budesonide, fluticasone propionate, beclometasone propionate ester, dexamethasone, dexamethasone acetate, dexamethasone palmitate, dexamethasone sodium metasulfobenzoate, dexamethasone sodium phosphate, triamcinolone, triamcinolone acetonide, hydrocortisone, hydrocortisone succinic acid ester sodium, fludrocortisone acetate, prednisolone, prednisolone succinic acid ester sodium, prednisolone sodium phosphate, beclometasone propionate ester, betamethasone, betamethasone d-chlorpheniramine maleic acid, betamethasone acetate, betamethasone sodium phosphate ester, betamethasone sodium phosphate ester, methylprednisolone, methylprednisolone sodium succinate or methylprednisolone acetate.

In one embodiment, the active pharmaceutical ingredient may comprise a therapeutic peptide or protein. Suitable therapeutic peptides and proteins comprise insulin, vasopressin and analogues, calcitonin, enkephalins, cyclosporines, oxytocin, Follicle-Stimulating Hormone (FSH), Luteinizing Hormone (LH), superoxydodismutase, interleukin 12 (IL-12), interferons, Colony Stimulating Factor (CSF), Tumor Necrosis Factor (TNF), Gonadotropin Releasing Hormone (GnRH)-antagonists, monoclonal antibodies, such as cetuximab, bevacizumab and also other non-protein drugs, for example chlorpromazine, ethinylestradiol, flurazepam and lorazepam, that undergo degradation when in contact with the gastro-intestinal enzymes.

In one embodiment, the active pharmaceutical ingredient may comprise a non-steroidal anti-inflammatory drugs (NSAID) comprising aceclofenac, acemetacin, aloxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, meloxicam, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, tolmetin, or valdecoxib.

In one embodiment, the active pharmaceutical ingredient may comprise a therapeutic agent useful for treating inflammatory bowel disease (Crohn's disease or ulcerative colitis). Exemplary non-limiting active pharmaceutical ingredients useful for the treatment of inflammatory bowel disease may comprise a 5-aminosalicylic acid drug such as mesalamine (e.g., Asacol®, Pentasa®, Rowasa®, Canasa®, or Lialda®) Olsalazine (e.g., Dipentum®) Balsalazide (e.g., Colazal®), or Sulfasalazine (e.g., Azulfidine®, Pyralin®, or Salazopyrin®); a steroid such as prednisone (Deltasone®), methylprednisolone (Medrol®), hydrocortisone (Cortef®), cortisol, or budesonide (Entecort®); an immunosuppressant such as azathioprine (Imuran® or Azasan®), 6-mercaptopurine (6-MP, Purixan®, or Purinethol®), cyclosporine A (Gengraf®, Sandimmune®, or Neoral®), tacrolimus)(Prograf®), or methotrexate (MTX®, Rheumatrex®, or Mexate®); a biologic TNF-alpha or integrin inhibitors such as infliximab (Remicade®), adalimumab (Humira®), golimumab (Simponi®), certolizumab (Cimzia®), vedolizumab (Entyvio®), ustekinumab (Stelara®), or natalizumab (Tysabri®), an antibiotic comprising a penicillin (e.g., amoxicillin, ampicillin, penicillin G), a quinolone (e.g., ciprofloxacin), or metronidazole (e.g., Flagyl®) or a combination of active pharmaceutical ingredients or therapeutic agents thereof.

In one embodiment, the active pharmaceutical ingredient may comprise a therapeutic agent useful for treating irritable bowel syndrome. Exemplary non-limiting active pharmaceutical ingredients useful for the treatment of irritable bowel syndrome comprise antidiarrheals such as atropine, diphenoxylate (Lomotil®), dicyclomine (Bentyl®), loperamide (Imodium®), rifaximin (Xifaxan®), alosetron (Lotronex®); bile acid binding agents such as cholestyramine (Prevailite®); constipation therapeutics such as linaclotide (Linzess®) or lubiprostone (Amitiza®) or a combination thereof.

In one embodiment, the active pharmaceutical ingredient may comprise a therapeutic agent useful for treating colon or colorectal cancer. Exemplary non-limiting active pharmaceutical ingredients useful for the treatment of colon or colorectal cancer comprise fluorouracil (Adrucil®, Efudex®, or Fluoroplex®), bevacizumab (Avastin®), irinotecan hydrochloride (Camptosar®), capecitabine (Xeloda®), cetuximab (Erbitux®), oxaliplatin (Eloxatin®), leucovorin calcium (Wellcovorin®), panitumumab (Vectibix®), regorafenib (Stivarga®), or aflibercept (Aleya®), or a combination of active pharmaceutical ingredients or therapeutic agents thereof.

In one embodiment, the active pharmaceutical ingredient may comprise a therapeutic agent that undergoes first pass metabolism. Exemplary non-limiting active pharmaceutical ingredients useful in the controlled release pharmaceutical compositions described herein that undergo first pass metabolism comprise chlorpromazine, aspirin, oestrogens, enalapril, lidocaine, lignocaine, prazepam, amitriptyline, nortriptyline, imipramine, pentazocine, pethidine, chlormethiazole, isosorbide dinitrate, glyceryl trinitrate, lignocaine, oxprenolol, propranolol, verapamil, or labetolol or a combination thereof.

In one embodiment, the active pharmaceutical ingredient may comprise a therapeutic agent that is poorly soluble or has a low solubility and has a low permeability (e.g., any BCS class IV compound). Exemplary non-limiting active pharmaceutical ingredients useful in the controlled release pharmaceutical compositions described herein comprise acetaminophen, acetazolamide, acyclovir, allopurinol, amoxicillin, cefdinir, cefixime, cefotiam hexetil hydrochloride, cefpodoxime proxetil, cefuroxime axetil, dapsone, dexamethasone, doxycycline, famotidine, fexofenadine, folic acid, furosemide, glipizide, griseofulvin, hydrochlorothiazide, 1-carbocysteine, levodopa, levosulpiride, linezolid, meloxicam, mesalamine, metoclopramide, modafinil, nabumetone, nalidixic acid, oxcarbazepine, oxycodone, phenobarbital, propylthiouracil, sulfadiazine, sulfamethoxazole, sultamicillin, theophylline, tosufloxacin, triflusal, trimethoprim, and zaltoprofen or pharmaceutically acceptable salts, isomers, prodrugs (e.g., esters) and derivatives thereof, and mixtures of any of the active pharmaceutical ingredients listed thereof.

In other embodiments, the pharmaceutical compositions as described herein are suitable for use for water soluble as well as slightly soluble or insoluble active drug substances.

In another embodiment, all of the above mentioned active drug substances may also be in the form of pharmaceutically acceptable salts, uncharged or charged molecules, molecular complexes, solvates, or anhydrates thereof, and, if relevant, single isomers, enantiomers, racemic mixtures, or mixtures thereof.

In another embodiment, the pharmaceutical compositions described herein may comprise pharmaceutically acceptable salts of any of the above mentioned active drug substances.

The term "pharmaceutically acceptable salts" of an active drug substance includes alkali metal salts such as, for example, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methanesulphonic acid, toluenesulphonic acid etc. In another embodiment, pharmaceutically acceptable opioid salts can comprise sulphate salts, hydrochloride salts, and bitartrate salts.

In another embodiment, the active pharmaceutical ingredient may be in any of its crystalline, polymorphous, semicrystalline, amorphous or polyamorphous forms or mixtures thereof.

The concentration of the active drug substance in the pharmaceutical composition for use according to the disclosure depends on the specific active drug substance, the disease to be treated, the condition of the patient, the age, and gender of the patient, etc. The above-mentioned active drug substances may be known active drug substances and a person skilled in the art will be able to find information as to the dosage of each active drug substance and, accordingly, will know how to determine the amount of each active drug substance in the pharmaceutical composition.

The active pharmaceutical ingredient may be a new chemical entity for which the amount of information is limited. In such cases, the dosage has to be evaluated based on available preclinical and/or clinical data.

In one embodiment described herein, the pharmaceutical composition comprises soft capsule shell comprising a matrix comprising an active pharmaceutical ingredient.

In one embodiment described herein, the soft capsule shell has the composition of Table 3, including all possible iterations of the specified ranges that provide 100% for the total weight percentage, including or excluding the optional colorings, flavorings, or excipients.

TABLE 3

Exemplary soft gelatin capsule composition

| Component | Exemplary Component | Weight Percentage (%) |
|---|---|---|
| Film-forming polymer | Gelatin | 25-50 |
| Plasticizer | Glycerol | 15-25 |
| Solvent | Water | 20-40 |
| Opacifier (optional) | Titanium dioxide | 0.5-1.5 |
| Coloring agent (optional) | Various | 0.05-0.1 |
| TOTAL | | 100% |

Film-former polymers that are useful for creating soft capsules as described herein are gelatin or hydroxypropyl-methylcellulose (HPMC). In one aspect, the film-forming polymer is gelatin.

Plasticizers that are useful for creating soft capsules as described herein are glycerol, sorbitol, polyethylene glycols, or combinations thereof. The weight ratio between the film-forming polymer, plasticizer, and solvent is adjusted so that the gel mass is flowable and not too viscous, and can be made into soft capsules using rotary die encapsulation methods.

In one embodiment, the enteric soft capsule shell has the exemplary composition shown in Table 4.

TABLE 4

Exemplary Soft Capsule Shell Composition

| Component | Percent weight (%) |
|---|---|
| Gelatin | 43 |
| Glycerol | 20 |
| Titanium dioxide (optional) | 0.7 |
| Coloring agent (optional) | 0.1 |
| Water | 36.2 |
| TOTAL | 100% |
| Final pH | ~4-7 |
| Ratio total plasticizer to gelatin | 20:43 (0.46:1) |
| Water content in dried soft capsule shell: | 8-15% |

In one embodiment described herein, the soft capsule comprises about 43% of at least one film-forming polymer; about 20% of at least one plasticizer; about 36% water; optionally, about 0.7% titanium dioxide; and optionally, about 0.1% of at least one coloring agent.

In one embodiment, the weight percentage range of film-forming polymer of the soft capsule described herein is about 35% to about 45%, including all integers within the specified range. In one aspect, the film-forming polymer weight percentage is about 38%. In another, the film-forming 1 polymer weight percentage is about 42%. In another aspect, the film-forming polymer weight percentage is about 44%.

In one embodiment, the weight percentage range of plasticizer is about 15% to about 22%, including all iterations of integers with the specified range. In one aspect, the plasticizer weight percentage is about 17%. In another aspect, the plasticizer weight percentage is about 18.5%. In another aspect, the plasticizer weight percentage is about 20%.

In one embodiment, the weight percentage ratio range of plasticizer to film-forming polymer is about 0.33:1 to about 0.56:1, including all iterations of iterations of ratios with the specified range. In one embodiment, the weight percentage ratio range of plasticizer to film-forming polymer is about 0.38:1. In one embodiment, the weight percentage ratio range of plasticizer to film-forming polymer is about 0.42:1. In one embodiment, the weight percentage ratio range of plasticizer to film-forming polymer is about 0.46:1. In one embodiment, the weight percentage ratio range of plasticizer to film-forming polymer is about 0.52:1.

In one aspect, soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing soft capsules comprising the pharmaceutical composition as described herein. The process includes preparing a gel mass composition comprising a film-forming, water-soluble polymer, an appropriate plasticizer, and solvent; casting the gel mass into films or ribbons using heat-controlled drums or surfaces; and manufacturing a soft capsule comprising a matrix fill using rotary die technology. The thickness of the films or ribbons that form the soft capsule shell is from about 0.010 inches (≈0.254 mm) to about 0.050 inches (≈1.27 mm), including all integers within the specified range. The shell thickness can be about 0.010 inch (≈0.254 mm), about 0.015 inch (≈0.381 mm), about 0.02 in (≈0.508 mm), about 0.03 in (≈0.762 mm), about 0.04 in (≈1.02 mm), or about 0.05 in (≈1.27 mm). In one embodiment, the thickness is about 0.02 inches (≈0.508 mm) to about 0.040 inches (≈1.02 mm). In one embodiment, the shell thickness is about 0.028 inches (≈0.711 mm). In another embodiment, the shell thickness is about 0.033 inches (≈0.838 mm). In another embodiment, the shell thickness is about 0.038 inches (≈0.965 mm).

In one embodiment described herein, the soft capsule shell described herein, encapsulates a matrix fill as described herein. In another embodiment described herein, the soft capsule shell and encapsulated matrix fill comprises an outer dimension from about 2 oval to about 30 oval including all iterations of capsule size within the specified range (e.g., 2 oval, 3 oval, 4 oval, 5 oval, 6 oval, 7 oval, 8 oval, 10 oval, 12 oval, 16 oval, 20, or 30 oval). In another embodiment described herein, the soft capsule shell and encapsulated matrix fill comprises an outer dimension from about 2 round to about 28 round including all iterations of capsule size within the specified range (e.g., 2 round, 3 round, 4 round, 5 round, 6 round, 7 round, 8 round, 10 round, 12 round, 16 round, 20 round or 28 round). In another embodiment described herein, the soft capsule shell and encapsulated matrix fill comprises an outer dimension from about 2 oblong to about 22 oblong including all iterations of capsule size within the specified range (e.g., 2 oblong, 3 oblong, 4 oblong, 5 oblong, 6 oblong, 7 oblong, 8 oblong, 10 oblong, 11 oblong, 12 oblong, 14 oblong, 16 oblong, 20 oblong, or 22 oblong). Dimension specifications of soft capsules and tablets are known to those skilled in the art. See *Remington's Essentials of Pharmaceutics*, Pharmaceutical Press Publishing Company, London, UK, 1st Edition, 2013, which is incorporated by reference herein for such teachings.

In another embodiment described herein, the pharmaceutical composition comprises an enteric soft capsule shell comprising a matrix fill comprising an active pharmaceutical ingredient.

Enteric soft capsules are described in International Patent Application Publication No. WO 2004/030658; U.S. Patent Application Publication No. US 2006/0165778; and U.S. Pat. No. 8,685,445, each of which is incorporated by reference herein for such teachings. The enteric soft capsule shell may comprise one or more film forming polymers, one or more enteric acid-insoluble polymers, one or more plasticizers, one or more alkali-neutralizing agents, one or more solvents, optionally one or more colorants, and optionally one or more flavorings or other conventionally accepted pharmaceutical excipients or additives.

All-natural enteric soft capsules are described in International Patent Application Publication No. WO 2007/075475, which is incorporated by reference herein for such teachings. Film-former polymers that are useful for creating enteric soft capsules are gelatin or hydroxypropylmethylcellulose (HPMC). In one aspect of the enteric soft capsule shell described herein, the film-forming polymer is gelatin.

Examples of enteric, acid-insoluble polymers are acrylic and methacrylate acid copolymers, cellulose acetate phthalate (CAP), cellulose acetate butyrate, hydroxypropylmethylcellulose phthalate (HPMCP), alginic acid salts such as sodium or potassium alginate, pectin, or shellac. Poly(methacylic acid-co-methyl methacrylate) anionic copolymers based on methacrylic acid and methyl methacrylate are particularly stable and are preferred in some embodiments. Poly(meth)acrylates (methacrylic acid copolymer), available under the trade name EUDRAGIT® (Evonik Industries AG, Essen, Germany), are provided as powder or aqueous dispersions. In one aspect, the methacrylic acid copolymer can be EUDRAGIT® L 30 D-55; EUDRAGIT® L 100-55; EUDRAGIT® L 100; EUDRAGIT® L 12.5; EUDRAGIT® S 100; EUDRAGIT® S 12.5; EUDRAGIT® FS 30 D; EUDRAGIT® E 100; EUDRAGIT® E 12.5; EUDRAGIT® E PO; EUDRAGIT® RL 100; EUDRAGIT® RL PO; EUDRAGIT® RL 30 D; EUDRAGIT® RL 12.5; EUDRAGIT® RS 100; EUDRAGIT® RS PO; EUDRAGIT® RS 30 D; EUDRAGIT® RS 12.5; EUDRAGIT® NE 30 D; EUDRAGIT® NE 40 D; EUDRAGIT® NM 30 D; or other poly(meth)acrylate polymers. In one aspect, the enteric polymer is EUDRAGIT® L 100, a methacrylic acid copolymer, Type A. Acid-insoluble polymer specifications are detailed in the United States Pharmacopoeia and in various monographs.

Plasticizers that are useful for creating enteric soft capsules as described herein are glycerol, sorbitol, polyethylene glycol, citric acid, citric acid esters, such as tri-ethyl citrate, or combinations thereof. The weight ratio between the film-forming polymer, the enteric acid-insoluble polymer, and plasticizer is adjusted so that the gel mass is flowable and not too viscous, and can be made into soft capsules using rotary die encapsulation methods.

In one embodiment, enteric soft capsule shell compositions can be made by dissolving the enteric acid-insoluble polymer in an aqueous solution of an alkali neutralizing agent such as ammonia, sodium hydroxide, potassium hydroxide, or liquid amines such as tri-ethanol amine or ethylene diamine. The amount of alkali is adjusted to give a final pH value of the gel mass less than or equal to about pH 9.0. In one embodiment, the final pH does not exceed 8.5. The volatile alkali neutralizing agent, ammonia is preferred. The film-forming polymer can then be combined with the plasticizer and solvent and then blended with the acid-insoluble gel to make a final homogeneous mix in a heat-controlled vessel and can be degassed by using vacuum. The fugitive ammonia evaporates during degassing. Using the foregoing process, the alkali concentrations do not require an additional step such as heating or neutralizing with acid in order to neutralize the gel mass.

In another embodiment described herein, an enteric soft capsule shell can be made by using an aqueous dispersion of the acid-insoluble polymer by adding alkaline materials such as ammonium, sodium, or potassium hydroxides, other alkalis, or a combination thereof that will cause the enteric acid-insoluble polymer to dissolve. The plasticizer-wetted, film-forming polymer can then be mixed with the solution of the acid-insoluble polymer. In one embodiment, enteric acid-insoluble polymers in the form of salts of the above-mentioned bases or alkalis can be dissolved directly in water and mixed with the plasticizer-wetted, film-forming polymer.

In one embodiment, an enteric soft capsule shell has the composition of Table 5, including all possible iterations of the specified ranges that provide 100% for the total weight percentage, including or excluding the optional, excipients, opacifiers, colorants, and flavorings.

TABLE 5

Exemplary Enteric Soft Capsule Shell Composition

| Component | Exemplary Component | Composition Range (%) |
|---|---|---|
| Film-forming polymer | Gelatin | 20-36 |
| Enteric, acid insoluble polymer | Methacrylic Acid Copolymer; Pectin | 2-20 |
| Plasticizer | Glycerol, Triethyl citrate | 15-22 |
| Alkali neutralizing agents (optional) | NH$_4$OH (30%), NaOH | 1-5 |
| Solvent | Water | 20-50 |
| Opacifier | Titanium Dioxide | 1-7.5 |
| Colorant (optional) | Various | 0.05-1 |
| Flavoring (optional) | Various | 0.05-2 |
| Excipients (optional) | Various | 1-5 |
| Gelling agent (optional) | Calcium, Magnesium, Potassium | 0.001-0.05 |

In one embodiment, an enteric soft capsule shell comprises a composition of about 30% film forming polymer; about 10% enteric, acid insoluble polymer; about 20% plasticizer; about 1% alkali neutralizing agent; and about 37% solvent. In one embodiment, an enteric soft capsule composition comprises a composition of about 30% to about 40% film-forming polymer; about 3% to about 5% enteric, acid insoluble polymer; about 13% to about 18% plasticizer; about 40% to about 48% water; and optionally about 0.005% to about 0.05% gelling agent.

In one embodiment, the weight percentage range of total polymer content (i.e., film forming polymer and enteric acid-insoluble polymer) of the enteric soft capsule described herein is about 30% to about 45%, including all integers within the specified range. In one aspect, the total polymer weight percentage is about 40%. In another aspect, the total polymer weight percentage is about 42%. In another aspect, the total polymer weight percentage is about 45%. In another aspect, the total polymer weight percentage is about 38%.

In one embodiment, the weight percentage range of total plasticizer is about 15% to about 22%, including all iterations of integers with the specified range. In one aspect, the total plasticizer weight percentage is about 19%. In another aspect, the total plasticizer weight percentage is about 17.7%. In another aspect, the total plasticizer weight percentage is about 18.9%. In another aspect, the total plasticizer weight percentage is about 19.3%.

In one embodiment, the alkali neutralizing-agent is ammonia (ammonium hydroxide; 30% w/v) that is added to comprise a weight percentage of about 1 to about 5% of the total enteric soft capsule composition. In one aspect, 30% w/v ammonia is added to comprise a weight percentage of about 2%. In another aspect, 30% w/v ammonia is added to a weight percentage of about 1.7%. In one aspect, ammonia is added to provide a final pH of about 9 in the enteric soft capsule composition. In another aspect, ammonia is added to provide a final pH of about 8.5 in the enteric soft capsule composition. In another aspect, after the capsules are filled and dried, the ammonia concentration is substantially reduced, owing to the fugitive nature of the volatile alkali. In one aspect, practically all of the ammonia is evaporated except for ammonium ions comprising salts with other moieties in the composition.

In one embodiment, the weight ratio range of film forming polymer to enteric acid insoluble polymer (film forming: enteric) is about 25:75 (≈0.33) to about 40:60 (≈0.67) (i.e., 0.33-0.67), including all iterations of ratios within the specified range. In one aspect, the ratio of film forming polymer to enteric acid insoluble polymer is about 30:70 (≈0.43). In another aspect, the ratio of film forming polymer to enteric acid insoluble polymer is about 28:72 (≈0.38).

In one embodiment, the weight ratio of total plasticizer to film forming polymer is about 20:40 to 21:30 (i.e., ≈0.5-0.7), including all iterations of ratios within the specified range. In one aspect, the weight ratio of total plasticizer to film forming polymer is about 20:40 (≈0.5). In another aspect, the weight ratio of total plasticizer to film forming polymer is about 21:30 (≈0.7). In another aspect, the weight ratio of total plasticizer to film forming polymer is about 19:29 (≈0.65). In another aspect, the weight ratio of total plasticizer to film forming polymer is about 19.3:29.2 (≈0.66).

In one embodiment, the weight ratio of total plasticizer to enteric acid insoluble polymer is about 1:1 to about 2:1 (≈1-2), including all iterations of ratios within the specified range. In one aspect, the weight ratio of total plasticizer to enteric acid insoluble polymer is about 11:10 (≈1.1). In another aspect, the weight ratio of total plasticizer to enteric acid insoluble polymer is about 14:10 (≈1.4). In another aspect, the weight ratio of total plasticizer to enteric acid insoluble polymer is about 17:10 (≈1.7). In another aspect, the weight ratio of total plasticizer to enteric acid insoluble polymer is about 20:10 (≈2). In another aspect, the weight ratio of total plasticizer to enteric acid insoluble polymer is about 19.3:11.2 (≈1.73).

In one embodiment, the weight ratio range of total plasticizer to total polymer (film forming and enteric acid insoluble polymer) is about 18:45 to about 20:40 (i.e., ≈0.40-0.5), including all iterations of ratios within the specified range. In one aspect, the weight ratio range of total plasticizer to total polymer is about 18:45 (≈0.40). In another aspect, the weight ratio range of total plasticizer to total polymer is about 19:40 (≈0.475). In another aspect, the weight ratio range of total plasticizer to total polymer is about 20:40 (≈0.5). In another aspect, the weight ratio range of total plasticizer to total polymer is about 19.3:40.4 (≈0.477).

In one embodiment, the solvent comprises about 20% to about 40% of the enteric soft capsule composition, including all integers within the specified range. In one embodiment, the solvent is water. The quantity of water in the composition varies depending on the quantities of the other ingredients. For example, the quantity of opacifier, colorant, flavoring, or other excipients can change the percentage of water present the composition. In one embodiment, the weight percentage of water is as much as suffices to bring the total weight percentage to 100% (i.e., quantum sufficiat; q.s.). In another embodiment, the water comprises about 20%, about 25%, about 30%, about 35%, or about 40% of the enteric soft capsule composition. In another embodiment, water comprises about 35% to about 40% of the enteric soft capsule composition. In one embodiment, water comprises about 37% of the composition.

In one embodiment, the final moisture (water) content of the enteric soft capsule is from about 8% to about 15%, including all integers within the specified range. In another embodiment, the moisture content is about 8% to about 12%, including all integers within the specified range. In one aspect, the final moisture content is about 8%. In one aspect, the final moisture content is about 9%. In one aspect, the final moisture content is about 10%. In one aspect, the final moisture content is about 11%. In another aspect, the final moisture content is about 12%.

In one embodiment, the enteric soft capsule shell has the exemplary composition shown in Table 6.

TABLE 6

Exemplary Enteric Soft Capsule Shell Composition

| Component | Percent weight |
| --- | --- |
| Gelatin | 29.2 |
| Methacrylic Acid Copolymer (EUDRAGIT ® L 100) | 11.2 |
| Glycerol | 18.0 |
| Triethyl citrate | 1.3 |
| Ammonium hydroxide | 1.7 |
| Titanium dioxide | 1.5 |
| Water | 37.1 |
| TOTAL | 100% |
| Final pH | ~4-9 |
| Total polymer % weight (gelatin + enteric) | 40.4% |
| Gelatin % wt of total polymer (gelatin + enteric) | 72.4% |
| Enteric % wt of total polymer (gelatin + enteric) | 27.6% |
| Ratio of Enteric to Gelatin | 11.2:29.2 (0.38) |
| Total plasticizer % weight (glycerol + triethyl citrate) | 19.3% |
| Ratio of total plasticizer to total polymer | 19.3:40.4 (0.48) |
| Ratio total plasticizer to gelatin | 19.3:29.2 (0.66) |
| Ratio total plasticizer to enteric | 19.3:11.2 (1.73) |
| Water content in dried enteric soft capsule: | 8-15% |

In one embodiment, the enteric soft capsule shell comprises about 30% gelatin; about 10% poly(methyl) acrylate copolymer; about 18% glycerol; about 1% triethyl citrate; about 1.5% ammonia; about 37% water; and about 1.5% titanium dioxide.

One embodiment described herein provides an enteric acid-insoluble polymer dispersed within the film-forming polymer gel mass that provides the total soft gel composition with enteric acid-insoluble properties, at relatively low concentrations of the enteric acid-insoluble polymer (e.g., from about 8% to about 20% of the total wet gel mass composition) and without the need of excessive amounts of alkali, thus avoiding denaturation or degradation of the film-forming polymer that can weaken the integrity of the enteric soft capsule shell.

In some embodiments, the enteric soft capsule shell does not dissolve or disintegrate in acids, such as 0.1 N hydrochloric acid or simulated gastric fluid (ca. pH 1.2), despite the fact that the majority of the shell ingredients (i.e., greater than 50%) normally dissolve in, or are miscible with, acids. In some embodiments, the enteric soft capsules made using the compositions described herein remain intact in hydrochloric acid or simulated gastric fluid for at least two hours and the capsules readily release their contents upon shifting the pH of the solution to ca. 6.8, such as that of simulated intestinal fluid. In one aspect, the enteric soft capsule is resistant to dissolution at about pH 1.2 for at least about 2 hours. In another aspect, the enteric soft capsule begins dissolution at pH of about 6.8 within about 10 min.

In another embodiment, the final enteric capsule composition provides films of increased strength without substantially compromising film elasticity. Moreover, films made from the enteric soft capsule compositions as described herein can be sealed at normal temperature range typically used for making traditional soft gel capsules. In one aspect, enteric soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing enteric soft capsules comprising the pharmaceutical composition as described herein. The process includes preparing a gel mass composition comprising a film-forming, water-soluble polymer and an enteric acid-insoluble polymer and mixing with appropriate plasticizers and solvent; casting the gel mass into films or ribbons using heat-controlled drums or surfaces; and manufacturing a soft capsule comprising a matrix fill using rotary die technology. The thickness of the films or ribbons that form the enteric capsule shell is from about 0.010 inches ($\approx$0.254 mm) to about 0.050 inches ($\approx$1.27 mm), including all integers within the specified range. The shell thickness can be about 0.010 inch ($\approx$0.254 mm), about 0.015 inch ($\approx$0.381 mm), about 0.02 in ($\approx$0.508 mm), about 0.03 in ($\approx$0.762 mm), about 0.04 in ($\approx$1.02 mm), or about 0.05 in ($\approx$1.27 mm). In one embodiment, the thickness is about 0.02 inches ($\approx$0.508 mm) to about 0.040 inches ($\approx$1.02 mm). In one embodiment, the shell thickness is about 0.028 inches ($\approx$0.711 mm). In another embodiment, the shell thickness is about 0.033 inches ($\approx$0.838 mm). In another embodiment, the shell thickness is about 0.038 inches ($\approx$0.965 mm).

In one embodiment described herein, the enteric soft capsule shell described herein, encapsulates a matrix fill as described herein. In another embodiment described herein, the enteric soft capsule shell and encapsulated matrix fill comprises an outer dimension from about 2 oval to about 30 oval including all iterations of capsule size within the specified range (e.g., 2 oval, 3 oval, 4 oval, 5 oval, 6 oval, 7 oval, 8 oval, 10 oval, 12 oval, 16 oval, 20, or 30 oval). In another embodiment described herein, the enteric soft capsule shell and encapsulated matrix fill comprises a outer dimension from about 2 round to about 28 round including all iterations of capsule size within the specified range (e.g., 2 round, 3 round, 4 round, 5 round, 6 round, 7 round, 8 round, 10 round, 12 round, 16 round, 20 round or 28 round). In another embodiment described herein, the enteric soft capsule shell and encapsulated matrix fill comprises an outer dimension from about 2 oblong to about 22 oblong including all iterations of capsule size within the specified range (e.g., 2 oblong, 3 oblong, 4 oblong, 5 oblong, 6 oblong, 7 oblong, 8 oblong, 10 oblong, 11, oblong, 12 oblong, 14 oblong, 16 oblong, 20 oblong, or 22 oblong). Dimension specifications of soft capsules and tablets are known to those skilled in the art. See Remington's *Essentials of Pharmaceutics*, Pharmaceutical Press Publishing Company, London, UK, $1^{st}$ Edition, 2013, which is incorporated by reference herein for such teachings.

The pharmaceutical composition described herein can comprise a soft capsule comprising a matrix fill that is liquid, semi-solid, or solid. Capsules prepared as described herein can contain a hydrophobic solution or suspension, such as vegetable oils or shortening, or waxes, or combinations thereof. The matrix can be formulated to prevent interaction with the capsule shell components and release the pharmaceutical composition at a specified rate.

One embodiment described herein, is a pharmaceutical composition comprising a matrix fill formulation comprising any of the formulations shown in the Tables or Examples described herein. Any of the components of the formulations shown in the Tables or Examples can be increased, decreased, combined, recombined, switched, or removed to provide for a formulation comprising about 100% by weight.

In another embodiment, the controlled release pharmaceutical composition described herein provides a dosage of an active pharmaceutical ingredient described herein. The dosage form can be administered, for example, to a subject, or a subject in need thereof. In one aspect, the subject is a mammal, or a mammal in need thereof. In one aspect, the subject is a human, or human in need thereof. In one aspect, the human or human in need thereof is a medical patient. In one aspect, the human subject is a child (~0-9 years old) or an adolescent (~10-17 years old). In one aspect, the subject is from 0 to 9 years of age. In another aspect, the human subject is from 10 to 17 years of age. In another aspect, the human subject is over 17 years of age. In another aspect, the human subject is an adult (>18 years of age).

The dosage form can be administered, for example, 1×, 2×, 3×, 4×, 5×, 6×, or even more times per day. One or more dosage form can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, 1 year, 2, years, 3 years, 4 years, 5 years, over 5 years, a decade, multiple decades, or even longer. One or more dosage forms can be administered at a regular interval until the subject or subject in need thereof, does not require treatment, prophylaxis, or amelioration of any disease or condition including but not limited to, pain.

In one embodiment, the pharmaceutical composition described herein is administered in multiple dosages simultaneously. For example, two or more identical dosages are administered at one time. In another embodiment, two or more different dosages are administered at one time. Such dual or different simultaneous doses can be used to provide an effective amount of the pharmaceutical composition to a subject in need thereof.

In one embodiment, the dosage may be administered to a human in need of management of mild, mild to moderate, moderate, moderate to severe, or severe inflammatory bowel disease (e.g., Crohn's disease or ulcerative colitis). In another embodiment, the dosage may be administered to a human in need of management of mild, mild to moderate, moderate, moderate to severe, or severe irritable bowel syndrome. In another embodiment, the dosage may be administered to a human in need of management of mild, mild to moderate, moderate, moderate to severe, or severe colon or colorectal cancer.

In one embodiment, the controlled release oral pharmaceutical composition described herein, comprises an active pharmaceutical ingredient of about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, or even more.

In another embodiment, the controlled release oral pharmaceutical composition described herein, comprises an active pharmaceutical ingredient in the range of about 20 mg to about 250 mg, about 30 mg to about 250 mg, about 40 mg to about 250 mg, about 50 mg to about 250 mg, about 60 mg to about 250 mg, about 70 mg to about 250 mg, about 80 mg to about 250 mg, about 90 mg to about 250 mg, about 100 mg to about 250 mg, about 110 mg to about 250 mg, about 120 mg to about 250 mg, about 130 mg to about 250 mg, about 140 mg to about 250 mg, about 150 mg to about 250 mg, about 160 mg to about 250 mg, about 170 mg to about 250 mg, about 180 mg to about 250 mg, about 190 mg to about 250 mg, about 200 mg to about 250 mg, about 210 mg to about 250 mg, about 220 mg to about 250 mg, about 230 mg to about 250 mg, about 240 mg to about 250 mg; about 250 mg to about 500 mg, about 260 mg to about 500 mg, about 270 mg to about 500 mg, about 280 mg to about 500 mg, about 290 mg to about 500 mg, about 300 mg to about 500 mg, about 310 mg to about 500 mg, about 320 mg to about 500 mg, about 330 mg to about 500 mg, about 340 mg to about 500 mg, about 350 mg to about 500 mg, about 360 mg to about 500 mg, about 370 mg to about 500 mg, about 380 mg to about 500 mg, about 390 mg to about 500 mg, about 400 mg to about 500 mg, about 410 mg to about 500 mg, about 420 mg to about 500 mg, about 430 mg to about 500 mg, about 440 mg to about 500 mg, about 450 mg to about 500 mg, about 460 mg to about 500 mg, about 470 mg to about 500 mg, about 480 mg to about 500 mg, or about 490 mg to about 500 mg, about 490 mg to about 500 mg, about 500 mg to about 750 mg, about 510 mg to about 750 mg, about 520 mg to about 750 mg, about 530 mg to about 750 mg, about 540 mg to about 750 mg, about 550 mg to about 750 mg, about 560 mg to about 750 mg, about 570 mg to about 750 mg, about 580 mg to about 750 mg, about 590 mg to about 750 mg, about 600 mg to about 750 mg, about 610 mg to about 750 mg, about 620 mg to about 750 mg, about 630 mg to about 750 mg, about 640 mg to about 750 mg, about 650 mg to about 750 mg, about 660 mg to about 750 mg, about 670 mg to about 750 mg, about 680 mg to about 750 mg, about 690 mg to about 750 mg, about 700 mg to about 750 mg, about 710 mg to about 750 mg, about 720 mg to about 750 mg, about 730 mg to about 750 mg, about 740 mg to about 750 mg, about 750 mg to about 1000 mg, about 760 mg to about 1000 mg, about 770 mg to about 1000 mg, about 780 mg to about 1000 mg, about 790 mg to about 1000 mg, about 800 mg to about 1000 mg, about 810 mg to about 1000 mg, about 820 mg to about 1000 mg, about 830 mg to about 1000 mg, about 840 mg to about 1000 mg, about 850 mg to about 1000 mg, about 860 mg to about 1000 mg, about 870 mg to about 1000 mg, about 880 mg to about 1000 mg, about 890 mg to about 1000 mg, about 900 mg to about 1000 mg, about 910 mg to about 1000 mg, about 920 mg to about 1000 mg, about 930 mg to about 1000 mg, about 940 mg to about 1000 mg, about 950 mg to about 1000 mg, about 960 mg to about 1000 mg, about 970 mg to about 1000 mg, about 980 mg to about 1000 mg, about 990 mg to about 1000 mg, about 1000 mg to about 1250 mg, about 1010 mg to about 1250 mg, about 1020 mg to about 1250 mg, about 1030 mg to about 1250 mg, about 1040 mg to about 1250 mg, about 1050 mg to about 1250 mg, about 1060 mg to about 1250 mg, about 1070 mg to about 1250 mg, about 1080 mg to about 1250 mg, about 1090 mg to about 1250 mg, about 1100 mg to about 1250 mg, about 1110 mg to about 1250 mg, about 1120 mg to about 1250 mg, about 1130 mg to about 1250 mg, about 1140 mg to about 1250 mg, about 1150 mg to about 1250 mg, about 1160 mg to about 1250 mg, about 1170 mg to about 1250 mg, about 1180 mg to about 1250 mg, about 1190 mg to about 1250 mg, about 1200 mg to about 1250 mg, about 1210 mg to about 1250 mg, about 1220 mg to about 1250 mg, about 1230 mg to about 1250 mg, about 1240 mg to about 1250 mg, about 1250 mg to about 1500 mg, about 1260 mg to about 1500 mg, about 1270 mg to about 1500 mg, about 1280 mg to about 1500 mg, about 1290 mg to about 1500 mg, about 1300 mg to about 1500 mg, about 1310 mg to about 1500 mg, about 1320 mg to about 1500 mg, about 1330 mg to about 1500 mg, about 1340 mg to about 1500 mg, about 1350 mg to about 1500 mg, about 1360 mg to about 1500 mg, about 1370 mg to about 1500 mg, about 1380 mg to about 1500 mg, about 1390 mg to about 1500 mg, about 1400 mg to about 1500 mg, about 1410 mg to about 1500 mg, about 1420 mg to about 1500 mg, about 1430 mg to about 1500 mg, about 1440 mg to about 1500 mg, about 1450 mg to about 1500 mg, about 1460 mg to about 1500 mg, about 1470 mg to about 1500 mg, about 1480 mg to about 1500 mg, or about 1490 mg to about 1500 mg.

In one embodiment described herein, the controlled release oral pharmaceutical composition described herein may comprise an active pharmaceutical ingredient load (e.g., drug load) of about 1% to about 90%, including all integers within the specified range. In one embodiment, the drug load can comprise about 1%, about 2%, about 2.5%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or even higher. In one aspect, the drug load is about 20%. In another aspect, the drug load is about 25%. In another aspect, the drug load is about 30%. In another aspect, the drug load is about 35%. In another aspect, the drug load is about 40%. In another aspect, the drug load is about 50%. In another aspect, the drug load is about 60%. In another aspect, the drug load is about 28%. In another aspect, the drug load is about 32%. In another aspect, the drug load is about 44%. In another aspect, the drug load is about 48%.

In one embodiment, the active pharmaceutical ingredient comprises 5-amino-2-hydroxybenzoic acid (≈5-aminosalicylic acid, 5-ASA) also referred to as mesalamine (mesalazine), or a salt, ether, ester, variant, or derivative thereof. See Prescribing Information for Lialda® 08/2013 (Shire US Inc.; available at: www.lialda.com), and Pentasa® 04/2014 (Shire US Inc.; available at: www.pentasaus.com) which are incorporated by reference herein for such teachings.

In one aspect, the dose of mesalamine is 20 mg. In another aspect, the dose of mesalamine is 25 mg. In another aspect, the dose of mesalamine is 50 mg. In another aspect, the dose of mesalamine is 75 mg. In another aspect, the dose of mesalamine is 100 mg. In another aspect, the dose of mesalamine is 150 mg. In another aspect, the dose of mesalamine is 200 mg. In another aspect, the dose of mesalamine is 250 mg. In another aspect, the dose of mesalamine is 250. In another aspect, the dose of mesalamine is 300. In another aspect, the dose of mesalamine is 350. In another aspect, the dose of mesalamine is 400. In another aspect, the dose of mesalamine is 450. In another aspect, the dose of mesalamine is 500. In another aspect, the dose of mesalamine is 550. In another aspect, the dose of mesalamine is 600. In another aspect, the dose of mesalamine is 650. In another aspect, the dose of mesalamine is 700. In another aspect, the dose of mesalamine is 750. In another aspect, the dose of mesalamine is 800. In another aspect, the dose of mesalamine is 850. In another aspect, the dose of mesalamine is 900. In another aspect, the dose of mesalamine is 950. In another aspect, the dose of mesalamine is 1000. In another aspect, the dose of mesalamine is 1050. In another aspect, the dose of mesalamine is 1100. In another aspect, the dose of mesalamine is 1150. In another aspect, the dose of mesalamine is 1200. In another aspect, the dose of mesalamine is 1250. In another aspect, the dose of mesalamine is 1300. In another aspect, the dose of mesalamine is 1350. In another aspect, the dose of mesalamine is 1400. In another aspect, the dose of mesalamine is 1450. In another aspect, the dose of mesalamine is 1550.

In another embodiment, the total dosage of mesalamine administered in a 24-hour period is about 20 mg to about 5000 mg per 24-hour period, including all integers within the specified range. In another embodiment, the total dosage of mesalamine administered in a 24-hour period is about 250 mg to about 5000 mg per 24-hour period, including all integers within the specified range. In one aspect, the total dosage of mesalamine administered in a 24-hour period is about 500 mg. In another aspect, the total dosage of mesalamine administered in a 24-hour period is about 750 mg. In another aspect, the total dosage of mesalamine administered in a 24-hour period is about 1000 mg. In another aspect, the total dosage of mesalamine administered in a 24-hour period is about 1250 mg. In another aspect, the total dosage of mesalamine administered in a 24-hour period is about 1500 mg. In another aspect, the total dosage of mesalamine administered in a 24-hour period is about 2000 mg. In another aspect, the total dosage of mesalamine administered in a 24-hour period is about 2500 mg. In another aspect, the total dosage of mesalamine administered in a 24-hour period is about 3000 mg. In another aspect, the total dosage of mesalamine administered in a 24-hour period is about 3500 mg. In another aspect, the total dosage of mesalamine administered in a 24-hour period is about 4000 mg. In another aspect, the total dosage of mesalamine administered in a 24-hour period is about 4500 mg. In another aspect, the total dosage of mesalamine administered in a 24-hour period is about 5000 mg. The dosage can contain a total amount of mesalamine effective for treatment, amelioration, prophylaxis, or reducing the onset of or symptoms stemming from an inflammatory bowel disease (e.g., Crohn's disease or ulcerative colitis).

In one embodiment, the recommended dosage is based upon the condition of the subject in need thereof. The subject can comprise a human or mammal in need thereof. In one aspect, the need is defined as a bowel disease bowel disease comprising inflammatory bowel disease (e.g., Crohn's disease or ulcerative colitis).

In another embodiment, the controlled release pharmaceutical composition as described herein has an in vitro dissolution rate at pH 1.2 less than about 2% to about 20% after about 60 minutes to about 300 minutes, including each integer within the specified ranges of dissolution and time.

In one aspect, the in vitro dissolution rate of the controlled release pharmaceutical composition at pH 1.2 is less than about 20% after about 120 minutes, less than about 20% after about 180 minutes, less than about 20% after about 240 minutes, less than about 20% after about 5 300. In one aspect, the in vitro dissolution rate of the controlled release pharmaceutical composition at pH 1.2 is less than about 10% after about 120 minutes, less than about 10% after about 180 minutes, less than about 10% after about 240 minutes, less than about 10% after about 300 minutes. In one aspect, the in vitro dissolution rate of the controlled release pharmaceutical composition at pH 1.2 is less than about 5% after about 120 minutes, less than about 5% after about 180 minutes, less than about 5% after about 240 minutes, less than about 5% after about 300 minutes. In one aspect, the in vitro dissolution rate of the controlled release pharmaceutical composition at pH 1.2 is less than about 2% after about 120 minutes, less than about 2% after about 180 minutes, less than about 2% after about 240 minutes, less than about 2% after about 300 minutes. In one aspect, the in vitro dissolution rate of the controlled release pharmaceutical composition at pH 1.2 is less than about 1% after about 120 minutes, less than about 1% after about 180 minutes, less than about 1% after about 240 minutes, less than about 1% after about 300 minutes.

In another embodiment, the controlled release pharmaceutical composition as described herein has an in vitro dissolution rate at pH 4.5 less than about 2% to about 20% after about 60 minutes to about 300 minutes, including each integer within the specified ranges of dissolution and time. In one aspect, the in vitro dissolution rate of the controlled release pharmaceutical composition at pH 4.5 is less than about 20% after about 120 minutes, less than about 20% after about 180 minutes, less than about 20% after about 240 minutes, less than about 20% after about 5 300. In one aspect, the in vitro dissolution rate of the controlled release pharmaceutical composition at pH 4.5 is less than about 10% after about 120 minutes, less than about 10% after about 180 minutes, less than about 10% after about 240 minutes, less than about 10% after about 300 minutes. In one aspect, the in vitro dissolution rate of the controlled release pharmaceutical composition at pH 4.5 is less than about 5% after about 120 minutes, less than about 5% after about 180 minutes, less than about 5% after about 240 minutes, less than about 5% after about 300 minutes. In one aspect, the in vitro dissolution rate of the controlled release pharmaceutical composition at pH 4.5 is less than about 2% after about 120 minutes, less than about 2% after about 180 minutes, less than about 2% after about 240 minutes, less than about 2% after about 300 minutes. In one aspect, the in vitro dissolution rate of the controlled release pharmaceutical composition at pH 4.5 is less than about 1% after about 120 minutes, less than about 1% after about 180 minutes, less than about 1% after about 240 minutes, less than about 1% after about 300 minutes.

In another embodiment, the controlled release pharmaceutical composition as described herein has an in vitro dissolution rate at pH 7.2 of about 50% after about 150 to about 480 minutes. In another aspect, the in vitro dissolution rate at pH 7.2 is about 50% after about 300 to about 480 minutes. In another aspect, the in vitro dissolution rate at pH 7.2 is about 50% after about 320 to about 420 minutes. In another aspect, the in vitro dissolution rate at pH 7.2 is about 50% after about 300 to about 400 minutes. In another aspect, the in vitro dissolution rate at pH 7.2 is about 50% after about 150 minutes. In another aspect, the in vitro dissolution rate at pH 7.2 is about 50% after about 170 minutes. In another aspect, the in vitro dissolution rate at pH 7.2 is about 50% after about 190 minutes. In another aspect, the in vitro dissolution rate at pH 7.2 is about 50% after about 210 minutes. In another aspect, the in vitro dissolution rate at pH 7.2 is about 50% after about 230 minutes. In another aspect, the in vitro dissolution rate at pH 7.2 is about 50% after about 250 minutes. In another aspect, the in vitro dissolution rate at pH 7.2 is about 50% after about 270 minutes. In another aspect, the in vitro dissolution rate at pH 7.2 is about 50% after about 290 minutes. In another aspect, the in vitro dissolution rate at pH 7.2 is about 50% after about 320 minutes. In another aspect, the in vitro dissolution rate at pH 7.2 is about 50% after about 340 minutes. In another aspect, the in vitro dissolution rate at pH 7.2 is about 50% after about 360 minutes. In another aspect, the in vitro dissolution rate at pH 7.2 is about 50% after about 380 minutes. In another aspect, the in vitro dissolution rate at pH 7.2 is about 50% after about 400 minutes. In another aspect, the in vitro dissolution rate at pH 7.2 is about 50% after about 420 minutes. In another aspect, the in vitro dissolution rate at pH 7.2 is about 50% after about 440 minutes. In another aspect, the in vitro dissolution rate at pH 7.2 is about 50% after about 480 minutes. In another aspect, the in vitro dissolution rate at pH 7.2 is about 50% after about 500 minutes.

Another embodiment described herein is a controlled release pharmaceutical composition as described herein for administration to a subject having a bowel disease comprising inflammatory bowel disease (e.g., Crohn's disease or ulcerative colitis), irritable bowel syndrome or colon or colorectal cancer comprising a therapeutically effective amount of one or more active pharmaceutical ingredients exhibiting an in vitro dissolution rate at pH 7.2 comprising about 20% to about 80% dissolution after about 60 min to about 840 min, including each integer within the specified ranges of dissolution and time. In another aspect, the in vitro dissolution rate at pH 7.2 is about 50% after about 60 min to about 480 min, including each integer with in the specified time range. In one aspect, the in vitro dissolution rate at pH 7.2 is about 50% after about 60 min, about 50% after about 70 min, about 50% after about 80 min, about 50% after about 90 min, about 50% after about 120 min, about 50% after about 150 min, about 50% after about 180 min, about 50% after about 210 min, about 50% after about 240 min, about 50% after about 300 min, is about 50% after about 330 min, about 50% after about 360 min, is about 50% after about 390 min, about 50% after about 420 min, about 50% after about 480 min, about 50% after about 540 min, about 50% after about 600 min, about 50% after about 660 min, about 50% after about 720 min, about 50% after about 780 min, about 50% after about 840 min, about 50% after about 900 min, about 50% after about 960 min, or about 50% after 1080 min.

Another embodiment described herein, is a controlled release oral pharmaceutical composition comprising a therapeutically effective amount of one or more active pharmaceutical ingredients, wherein the pharmaceutical composition dissolves along the small intestine. In one aspect the pharmaceutical composition does not dissolve in the stomach and begins dissolving in the small intestine. In another aspect, about 5% to about 25% of the active pharmaceutical ingredient(s) is released along the entire length of the small intestine, including each integer within the specified range. In another aspect the pharmaceutical composition begins dissolving in the small intestine and about 25% to about 50% of the active pharmaceutical ingredient(s) is released along the entire length of the small intestine, including each integer within the specified range. In another aspect about 50% to about 75% of the active pharmaceutical ingredient(s) is released along the entire length of the small intestine, including each integer within the specified range. In another aspect, about 75% to greater than about 90% of the active pharmaceutical ingredient(s) is released along the entire length of the small intestine, including each integer within the specified range. In another aspect, the release of the active pharmaceutical ingredient is localized in one area and is not released along the entire length of the small intestine.

Another embodiment described herein, is a controlled release oral pharmaceutical composition comprising a therapeutically effective amount of one or more active pharmaceutical ingredients, wherein the pharmaceutical composition dissolves along the length of the colon. In one aspect the pharmaceutical composition does not dissolve in the stomach or small intestine and begins dissolving in the colon. In another aspect, about 5% to about 25% of the active pharmaceutical ingredient(s) is released along the entire length of the colon, including each integer within the specified range. In another aspect, about 25% to about 50% of the active pharmaceutical ingredient(s) is released along the entire length of the colon, including each integer within the specified range. In another aspect about 50% to about 75% of the active pharmaceutical ingredient(s) is released along the entire length of the colon, including each integer within the specified range. In another aspect, about 50% to about 75% of the active pharmaceutical ingredient(s) is released along the entire length of the colon, including each integer within the specified range. In another aspect, about 75% to greater than about 90% of the active pharmaceutical ingredient(s) is released along the entire length of the colon, including each integer within the specified range. In another aspect, the release of the active pharmaceutical ingredient is localized in one area and is not released along the entire length of the colon.

Another embodiment described herein is a controlled release pharmaceutical composition as described herein comprising a therapeutically effective amount of one or more active pharmaceutical ingredients for administration to a subject having a bowel disease comprising inflammatory bowel disease (e.g., Crohn's disease or ulcerative colitis), irritable bowel syndrome or colon or colorectal cancer exhibiting less than about a 2% to about a 20% dissolution rate at pH 1.2 after about 60 minutes to about 300 minutes; less than about a 2% to about a 20% dissolution rate at pH 4.5 after about 60 minutes to about 300 minutes; and about a 50% in vitro dissolution rate at pH 7.2 after about 60 minutes to about 480 minutes.

Another embodiment described herein is a controlled release pharmaceutical composition as described herein comprising a therapeutically effective amount of one or more active pharmaceutical ingredients for administration to a subject in need thereof, exhibiting an in vitro dissolution rate as described herein in any one of Drawings 1-2.

Another embodiment described herein is a method for orally administering a dosage form of a controlled release pharmaceutical composition comprising an active pharmaceutical ingredient described herein to the colon or along the length of the colon for the treatment, amelioration, prophylaxis, or reducing the onset of or symptoms stemming from a bowel disease comprising inflammatory bowel disease (e.g., Crohn's disease or ulcerative colitis), irritable bowel syndrome or colon or colorectal cancer.

Another embodiment described herein is a method for orally administering a dosage form of a controlled release pharmaceutical composition comprising an active pharmaceutical ingredient described herein along to the small intestine or along the length of the small intestine for the treatment, amelioration, prophylaxis, or reducing the onset of or symptoms stemming from a bowel disease comprising inflammatory bowel disease (e.g., Crohn's disease or ulcerative colitis), irritable bowel syndrome or colon or colorectal cancer.

Another embodiment described herein is a method for treating, retarding the progression of, delaying the onset of, prophylaxis of, amelioration of, or reducing the symptoms of a bowel disease comprising inflammatory bowel disease (e.g., Crohn's disease or ulcerative colitis), irritable bowel syndrome or colon or colorectal cancer comprising administering to a subject in need there of a controlled release pharmaceutical composition as described herein comprising a therapeutically effective amount of one or more active pharmaceutical ingredients, wherein the pharmaceutical composition exhibits less than about a 2% to about a 20% dissolution rate at pH 1.2 after about 60 minutes to about 300 minutes; less than about a 2% to about a 20% dissolution rate at pH 4.5 after about 60 minutes to about 300 minutes; and about a 50% in vitro dissolution rate at pH 7.2 after about 60 minutes to about 480 minutes.

Another embodiment described herein is a method for treating, retarding the progression of, delaying the onset of, prophylaxis of, amelioration of, or reducing the symptoms of a bowel disease comprising inflammatory bowel disease (e.g., Crohn's disease or ulcerative colitis), irritable bowel syndrome or colon or colorectal cancer comprising administering to a subject in need there of a controlled release pharmaceutical composition as described herein comprising a therapeutically effective amount of one or more active pharmaceutical ingredients wherein the pharmaceutical composition exhibits an in vitro dissolution rate as described herein in any one of Drawings 1-2.

Another embodiment described herein is a method for treating, retarding the progression of, delaying the onset of, prophylaxis of, amelioration of, or reducing the symptoms of a bowel disease comprising inflammatory bowel disease (e.g., Crohn's disease or ulcerative colitis), comprising the administration of a therapeutically effective amount of one or more the controlled release pharmaceutical compositions comprising mesalamine, wherein the administration is sufficient to achieve a reduction in symptoms or disease remission in the subject without substantially inducing one or more side effects including, renal impairment, such as interstitial nephritis; headache, gastrointestinal disorders, such as flatulence, cholecystitis, perforated peptic ulcers, gastrointestinal bleeding, colitis, nausea, pancreatitis, rectal polyps, or vomiting; pains, such as abdominal pain, pharyngolaryngeal pain, ear pain, or back pain; abdominal distention, dyspepsia, arthralgia, fatigue, hypertension, tachycardia, abnormal liver function, or skin disorders, such as psoriasis, pyoderma gangrenosum, erythema nodosum, alopecia, pruritus, rash, acne, or urticaria, hepatic impairement such as jaundice, cholestatic jaundice, hepatitis, liver necrosis, or liver failure; hematologic impairement, such as agranulocytosis or aplastic anemia; immune system disorders such as anaphylactic reactions, Stevens-Johnson syndrome (SJS), or drug reactions with eosinophilia and systemic symptoms (DRESS), peripheral neuropathy, Guillain-Barre syndrome, or transverse myelitis or reversible oligospermia or any combination of adverse side effects thereof. In one aspect, the occurence rate of any side effects is less than 10%, less than 9%, less than 8%, less than 7%, less than 6%, less than 5%, less than 4%, less than 3%, less than 2%, or even less than 1%. In another aspect, substantially no side effects are experienced after administration of the controlled release pharmaceutical compositions comprising mesalamine described herein.

In another embodiment, the controlled release pharmaceutical composition described herein is contained and dispensed from a tamper evident packaging. The term "tamper evident" or "tamper resistant" refers to a packaging of any kind that readily displays or allows for an individual to observe any physical interference or manipulation of said packaging. The tamper evident packaging provides reasonable evidence to consumers that tampering has occurred. The tamper evident packaging additionally contains appropriate labelling statements describing the features and evidences of the tamper evident packaging. In one aspect, the tamper evident packaging comprises: bottles, film wrappers, blister or strip packs, bubble packs, heat shrink bands or wrappers, foil, paper, or plastic pouches, container mouth inner seals, tape seals, breakable caps, sealed metal tubes or plastic heat-sealed tubes, sealed cartons, aerosol containers, cans including metal and composite materials, or any combination thereof. The packaging may also contain appropriate instructions for prescribing, instructions for use, warnings, or other appropriate information.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

EXAMPLES

Example 1

Controlled released matrices as described herein suitable for delivery to the colon were prepared using the composition shown in Table 7. The composition was prepared according to the method of Example 3 and encapsulated in a soft capsule shell.

TABLE 7

Exemplary Controlled Release Matrix Composition

| Ingredient | % Weight | | | | |
|---|---|---|---|---|---|
| | F1 | F2 | F3 | F4 | F5 |
| Oleic Acid | 48 | 53.759 | 49 | 46 | 44 |
| Gelucire ® 43/01 | 12 | 5.655 | 12 | 14 | 16 |
| Lutrol ® 127u | 7 | 3.992 | 7 | 7 | 7 |
| Kollidon ® SR | 5 | 1.996 | 5 | 5 | 5 |
| Carbopol ® 971 P | 3 | 1.331 | 1 | 3 | 3 |
| EUDRAGIT ® EPO | — | — | 1 | — | — |
| Mesalamine | 25 | 33.267 | 25 | 25 | 25 |
| TOTAL | 100 | 100 | 100 | 100 | 100 |

Example 2

An exemplary controlled release matrix composition as described herein comprises a liquid lipophilic vehicle, a semisolid lipophilic vehicle, a non-ionic surfactant, a hygroscopic polymer, one or more pH buffering agents, one or more hydrophilic polymers, and an active pharmaceutical ingredient. The controlled release matrices described herein comprise one or more semi-solid lipophilic vehicles, one or more hygroscopic polymers, one or more hydrophilic polymers, a suspension agent, and an active pharmaceutical ingredient. The process for preparing an controlled release matrix includes preparing a composition of one or more lipid or lipophilic vehicles, one or more hygroscopic polymers, one or more hydrophilic polymers, optionally one or more non-ionic surfactant, optionally one or more pH buffering agent(s), optionally one or more suspension agents, and one or more active pharmaceutical ingredient by heating said mixture from between 45° C. and 80° C. with stirring or agitation in a suitable vessel. The process further comprises decreasing the matrix mixture temperature to between about 25° C. and about 45° C. followed by a homogenization step, wherein the matrix is homogenized to be substantially flowable. Prior to encapsulation in a soft gel capsule described herein, the matrix is deaerated at a temperature of about 25° C. to about 45° C.

The process for manufacturing a soft capsule comprising the pharmaceutical composition as described herein includes preparing a gel mass for a soft capsule; casting the gel mass into films or ribbons using heat-controlled drums or surfaces; and manufacturing a soft capsule comprising a matrix fill using rotary die technology. During this process, the controlled release matrix is injected in to the lumen as the soft capsule is formed by rotary die encapsulation. The soft capsule can be a typical soft capsule ("soft gel") or an enteric soft capsule.

Example 3

The controlled release matrix compositions shown in Table 7 generated by the methods described herein and encapsulated in an enteric soft gel capsule as described herein, were tested on their respective dissolution kinetics and compared to a reference standard pharmaceutical containing 5-aminosalicyclic acid.

As shown in FIG. 1, the controlled release oral pharmaceutical compositions of Table 7 demonstrate controlled release properties across three different pH ranges. Samples were taken and the percentage of 5-aminosalicyclic acid (≈5-ASA) released from the matrix was assessed over a time period of 12 hours during agitation in a buffer at pH 1.2, pH 4.5, and pH 7.2 with paddles at 100 RPM. In one aspect, the reference 5-ASA tablet was subjected to enzymatic degradation and compared to the non-enzymatic dissolution profiles.

Example 4

The controlled release matrix compositions shown in Table 7 generated by the methods described herein and encapsulated in an enteric soft gel capsule as described herein, were tested on their respective dissolution kinetics.

Figure 2:
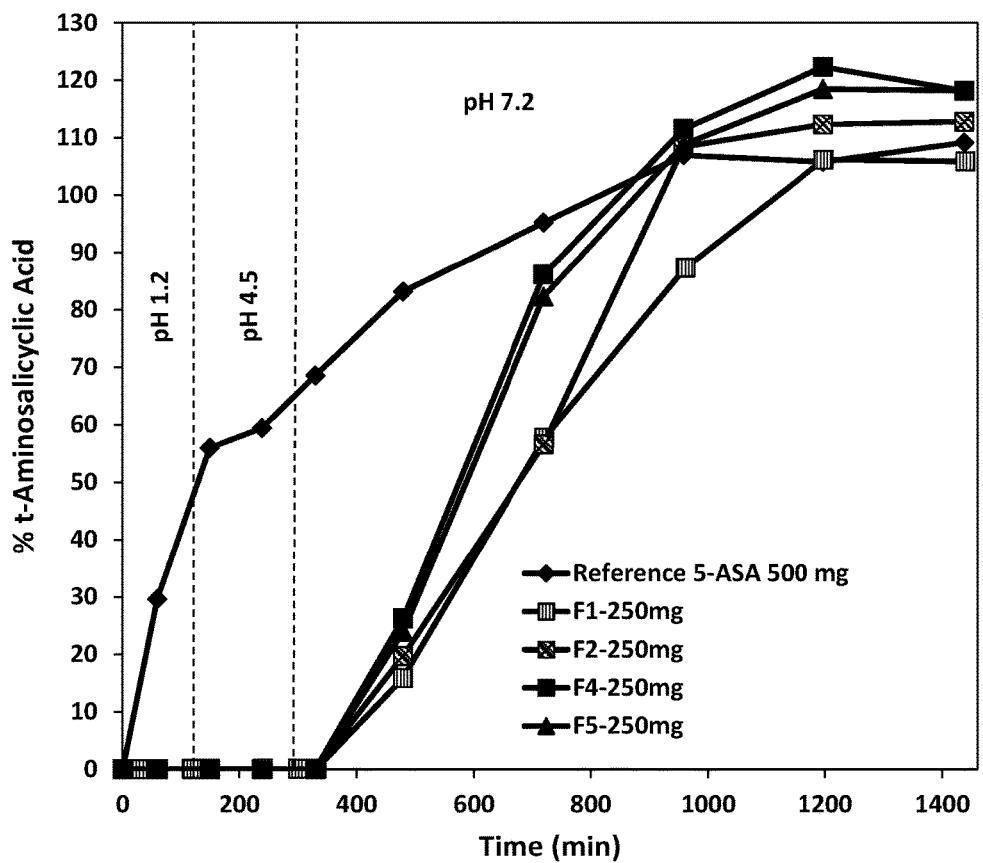
FIG. 2. Release profile of an enteric soft capsule comprising the compositions of Table 7 compared to reference tablets.

As shown in FIG. 2, the oral compositions of Table 7 demonstrate controlled release properties across 3 different pH ranges. Samples were taken and the percentage of 5-aminosalicyclic acid (5-ASA) released from the matrix was assessed over a time period of 12 hours during agitation in a buffer at pH 1.2, pH 4.5, and pH 7.2 with paddles at 100 RPM.

Example 5

Additional exemplary gel mass compositions useful for producing controlled release soft gel capsules as described herein are shown in Tables 8-11. Composition components are set forth by weight percentage of the total weight of the gel mass composition. Such compositions may be encapsulated in soft capsules or enteric soft capsules.

TABLE 8

Exemplary Controlled release Matrix Fills

| Ingredient | Weight Percentage (%) | | | | | |
|---|---|---|---|---|---|---|
| | EX 1 | EX 2 | EX 3 | EX 4 | EX 5 | EX 6 |
| Total Lipophilic Vehicle (TLV) | 54.0 | 60.0 | 63.0 | 59.0 | 54.5 | 57.2 |
| Non-ionic Surfactant (NIS) | 8 | 2 | 5 | 8 | 9.5 | 5 |
| Hygroscopic Polymer (HP) | 7 | 4 | 3 | 4 | 7 | 3 |
| Total Hydrophilic Polymer (THP) | 6.0 | 1.0 | 4.0 | 4.0 | 4.0 | 1.8 |
| Active Pharmaceut. Ingredient (API) | 25 | 33 | 25 | 25 | 25 | 33 |
| TOTAL | 100 | 100 | 100 | 100 | 100 | 100 |
| Components and Relational ratios | | | | | | |
| Hydrophilic Matrix Comp. (HMC) | 21.0 | 7.0 | 12.0 | 16.0 | 20.5 | 9.8 |
| Total Matrix Mass | 75.0 | 67.0 | 75.0 | 75.0 | 75.0 | 67.0 |
| Ratio Liquid to Semisolid Lipid | 3.2 | 11.0 | 4.3 | 2.1 | 2.3 | 6.9 |
| Ratio NIS to HP | 1.1 | 0.5 | 1.7 | 2.0 | 1.4 | 1.7 |
| Ratio of Anionic Pol. to Cationic Pol. | 1.0 | — | 0.3 | 3.0 | — | — |
| Ratio of TLV to HP + NIS | 3.6 | 10.0 | 7.9 | 4.9 | 3.3 | 7.2 |
| Ratio of TLV to HMC | 2.6 | 8.6 | 5.3 | 3.7 | 2.7 | 5.8 |
| Ratio of API to HMC | 1.2 | 4.7 | 2.1 | 1.6 | 1.2 | 3.4 |
| Ratio of API to TLV | 0.5 | 0.6 | 0.4 | 0.4 | 0.5 | 0.6 |
| Ratio API to Total Matrix | 0.3 | 0.5 | 0.3 | 0.3 | 0.3 | 0.5 |

TABLE 9

Exemplary Controlled release Matrix Fills

| Ingredient | Weight Percentage (%) | | | | | |
|---|---|---|---|---|---|---|
| | EX 1 | EX 2 | EX 3 | EX 4 | EX 5 | EX 6 |
| Total Lipophilic Vehicle (TLV) | 55.4 | 41.0 | 43.0 | 51.0 | 85.0 | 65.0 |

TABLE 9-continued

Exemplary Controlled release Matrix Fills

Weight Percentage (%)

| Ingredient | EX 1 | EX 2 | EX 3 | EX 4 | EX 5 | EX 6 |
|---|---|---|---|---|---|---|
| Non-ionic Surfactant (NIS) | 6.0 | 1.0 | 8.0 | 2.0 | 3.0 | 10.0 |
| Hygroscopic Polymer (HP) | 4.7 | 5.0 | 4.0 | 10.0 | 1.0 | 5.0 |
| Total Hydrophilic Polymer (THP) | 4.8 | 3.0 | 20.0 | 2.0 | 6.0 | 5.0 |
| Active Pharmaceut. Ingredient (API) | 29.2 | 50.0 | 25.0 | 35.0 | 5.0 | 15.0 |
| TOTAL | 100 | 100 | 100 | 100 | 100 | 100 |

Components and Relational ratios

| | EX 1 | EX 2 | EX 3 | EX 4 | EX 5 | EX 6 |
|---|---|---|---|---|---|---|
| Hydrophilic Matrix Comp. (HMC) | 15.4 | 9.0 | 32.0 | 14.0 | 10.0 | 20.0 |
| Total Matrix Mass | 70.8 | 50.0 | 75.0 | 65.0 | 95.0 | 85.0 |
| Ratio Liquid to Semisolid Lipid | 3.0 | 3.1 | 4.4 | 4.1 | 3.3 | 4.0 |
| Ratio NIS to HP | 1.3 | 0.2 | 2.0 | 0.2 | 3.0 | 2.0 |
| Ratio of Anionic Pol. to Cationic Pol. | 0.4 | — | 0.7 | — | 5.0 | 0.3 |
| Ratio of TLV to HP + NIS | 5.2 | 6.8 | 3.6 | 4.3 | 21.3 | 4.3 |
| Ratio of TLV to HMC | 3.6 | 4.6 | 1.3 | 3.6 | 8.5 | 3.3 |
| Ratio of API to HMC | 1.9 | 5.6 | 0.8 | 2.5 | 0.5 | 0.8 |
| Ratio of API to TLV | 0.5 | 1.2 | 0.6 | 0.7 | 0.1 | 0.2 |
| Ratio API to Total Matrix | 0.4 | 1.0 | 0.3 | 0.5 | 0.1 | 0.2 |

TABLE 10

Exemplary Controlled release Matrix Compositions

Weight Percentage (%)

| Ingredient | EX 1 | EX 2 | EX 3 | EX 4 | EX 5 | EX 6 |
|---|---|---|---|---|---|---|
| Oleic Acid | 41 | 55 | 51 | 40 | 38 | 50 |
| Gelucire ® 43/01 | 13 | 5 | 12 | 19 | 16.5 | 7.2 |
| Lutrol ® 127u | 8 | 2 | 5 | 8 | 9.5 | 5 |
| Kollidon ® SR | 7 | 4 | 3 | 4 | 7 | 3 |
| Carbopol ® 971 P | 3 | 1 | 1 | 3 | 4 | 1.8 |
| EUDRAGIT ® EPO | 3 | — | 3 | 1 | — | — |
| Active Pharmaceut. Ingredient (API) | 25 | 33 | 25 | 25 | 25 | 33 |
| TOTAL | 100 | 100 | 100 | 100 | 100 | 100 |

TABLE 11

Exemplary Controlled release Matrix Compositions

Weight Percentage (%)

| Ingredient | EX 1 | EX 2 | EX 3 | EX 4 | EX 5 | EX 6 |
|---|---|---|---|---|---|---|
| Oleic Acid | 41.4 | 31.0 | 35.0 | 41.0 | 65.0 | 52.0 |
| Gelucire ® 43/01 | 14.0 | 10.0 | 8.0 | 10.0 | 20.0 | 13.0 |
| Lutrol ® 127u | 6.0 | 1.0 | 8.0 | 2.0 | 3.0 | 10.0 |
| Kollidon ® SR | 4.7 | 5.0 | 4.0 | 10.0 | 1.0 | 5.0 |
| Carbopol ® 971 P | 1.3 | 3.0 | 8.0 | 2.0 | 5.0 | 1.0 |
| EUDRAGIT ® EPO | 3.5 | — | 12.0 | — | 1.0 | 4.0 |
| Active Pharmaceut. Ingredient (API) | 29.2 | 50.0 | 25.0 | 35.0 | 5.0 | 15.0 |
| TOTAL | 100 | 100 | 100 | 100 | 100 | 100 |

What is claimed is:

1. An oral pharmaceutical dosage form comprising a soft capsule shell and a flowable matrix comprising:
   (a) about 40% to about 55% by weight oleic acid;
   (b) about 1% to about 6% by weight carbomer polymer;
   (c) about 2% to about 8% by weight of polyvinylpyrrolidone;
   (d) about 1% to about 10% by weight of a poly(ethylene glycol)-block-poly(propylene glycol)-block-poly(ethylene glycol) non-ionic surfactant; and
   (e) about 25% to about 33% by weight of mesalamine;
   wherein the matrix dissolves in the colon.

2. The composition of claim 1, wherein the soft capsule shell comprises:
   (a) a film forming polymer;
   (b) a plasticizer; and
   (c) a solvent.

3. The composition of claim 2, wherein the soft capsule shell is an enteric soft capsule shell further comprising:
   (F) an enteric acid insoluble polymer; and
   (g) an alkali neutralizing agent.

4. The composition of claim 3, wherein the enteric soft capsule shell comprises: gelatin, a methacrylic acid copolymer, glycerol, triethyl citrate, ammonium hydroxide, and water.

* * * * *